(12) United States Patent
Feuerstein et al.

(10) Patent No.: US 8,053,247 B2
(45) Date of Patent: Nov. 8, 2011

(54) METHOD AND DEVICE FOR PREPARING AN ANALYTE FOR ANALYSIS BY MASS SPECTROMETRY

(75) Inventors: Isabel Feuerstein, Innsbruck (AT); Günther Bonn, Zirl (AT); Douglas T. Gjerde, Saratoga, CA (US); Christian Huck, Innsbruck (AT); Guenther Stecher, Götzens (AT)

(73) Assignee: PhyNexus, Inc., San Jose, CA (US)

( * ) Notice: Subject to any disclaimer, the term of this patent is extended or adjusted under 35 U.S.C. 154(b) by 744 days.

(21) Appl. No.: 11/973,912

(22) Filed: Oct. 10, 2007

(65) Prior Publication Data

US 2008/0090295 A1 Apr. 17, 2008

Related U.S. Application Data

(60) Provisional application No. 60/851,153, filed on Oct. 11, 2006.

(51) Int. Cl.
*G01N 1/00* (2006.01)
*G01N 1/18* (2006.01)

(52) U.S. Cl. .......... 436/174; 436/43; 436/178; 436/180; 422/68.1; 422/82.01; 422/82.05; 422/100

(58) Field of Classification Search .................... 436/43, 436/178, 174, 180; 422/68.1, 82.01, 82.05, 422/100
See application file for complete search history.

(56) References Cited

U.S. PATENT DOCUMENTS

| | | | |
|---|---|---|---|
| 6,197,498 B1 * | 3/2001 | Koster | 435/5 |
| 6,569,385 B1 | 5/2003 | Little et al. | |
| 6,897,072 B1 | 5/2005 | Rich et al. | |
| 2004/0009567 A1 * | 1/2004 | Duewel et al. | 435/183 |
| 2004/0033530 A1 | 2/2004 | Awrey et al. | |
| 2004/0214338 A1 | 10/2004 | Borchers | |
| 2006/0094065 A1 | 5/2006 | Lopez-Avila | |
| 2007/0224688 A1 | 9/2007 | Feuer et al. | |

OTHER PUBLICATIONS

JB Fenn et al. Electrospray ionization for mass spectrometry of large biomolecules. 1989 Science, vol. 246, Issue 4926, 64-71.
Karas and Hillenkamp. Laser desorption ionization of proteins with molecular masses exceeding 10,000 daltons. Anal. Chem., 60, 2299, 1995.
JA Loo. Bioanalytical mass spectrometry: many flavors to choose. Bioconjug Chem. Nov.-Dec. 1995;6(6):644-65.
P Chaurand et al. J Am Soc Mass Spectrom. Feb. 1999;10(2):91-103.
JA Loo et al. Analytical Chemistry vol. 65, Issue 4, 1993, pp. 425-438.
Feuerstein et al. Derivatized cellulose combined with MALDI-TOF-MS—a new tool for serum-protein profiling. 2005 J. Proteome Res. 4:2320-2326.
CR Lombardo et al. Biochemistry, 1995, 34(50), pp. 16456-16466.
NH Aprilita et al. Poly(glycidyl methacrylate/divinylbenzene)-IDA-FeIII in phosphoproteomics. J Proteome Res. Nov.-Dec. 2005;4(6):2312-9.
I Feuerstein et al. J Am Soc Mass Spectrom. Sep. 2006;17(9):1203-8.

(Continued)

*Primary Examiner* — Brian J Sines

(74) *Attorney, Agent, or Firm* — Sue S. Kalman

(57) ABSTRACT

The invention provides methods and apparatus for automated sample preparation for MALDI-TOF MS using columns in combination with a liquid handling system. The samples are typically biological such as serum or urine. The columns typically include a bed of media positioned within a modified pipette tip. In some embodiments, the invention provides methods for storing the prepared samples.

13 Claims, 12 Drawing Sheets

OTHER PUBLICATIONS

DK Ornstein et al. Journal of Urology Oct. 2004 vol. 172:1302-1305.
JH Lee et al. Journal of the American Society for Mass Spectrometry vol. 16, Issue 9, Sep. 2005, pp. 1456-1460.
K Turney et al. Rapid Communications in Mass Spectrometry. vol. 18, Issue 20, pp. 2367-2374, Oct. 30, 2004.
HJ Issaq et al. Biochem Biophys Res Commun. Apr. 5, 2002;292(3):587-92.
M. Najam-Ul-Haq et al. Analytica Chimica Acta. vol. 561, Issues 1-2, Mar. 2, 2006, pp. 32-39.
E. Orvisky et al. Proteomics 6 (2006): 2895-2902.
C.S. Raska et al. J Am Soc Mass Spectrom 2003, 14, 1076-1085.
L. Trojer et al. Rapid Communications in Mass Spectrometry vol. 19, Issue 22, pp. 3398-3404, Nov. 30, 2005.

* cited by examiner

MALDI Protein Profiles

METHOD AND DEVICE FOR PREPARING AN ANALYTE FOR ANALYSIS BY MASS SPECTROMETRY

CROSS REFERENCE TO RELATED APPLICATIONS

This application claims priority to and benefit of U.S. Provisional Patent Application No. 60/851,153 filed Oct. 11, 2006; U.S. patent application Ser. No. 10/434,713 filed May 8, 2003 and U.S. patent application Ser. No. 10/620,155, filed Jul. 14, 2003, the disclosures of which are incorporated herein by reference in their entirety for all purposes.

FIELD OF THE INVENTION

This invention relates to methods and devices for preparing an analyte from a sample solution for analysis by mass spectrometry. The analytes can include biomolecules, particularly biological macromolecules such as proteins, peptides, phosphopeptides, metabolites, lipids, nucleic acids, protein nucleic acid complexes, organic molecules and carbohydrates. The device and method of this invention are particularly useful in proteomics for sample preparation and analysis with analytical technologies employing MALDI mass spectrometry and other instrumentation.

BACKGROUND OF THE INVENTION

In many cases cancer can be cured when detected at an early, organ-confined stage. To facilitate early detection, there are considerable efforts do develop new biomarkers that improve current diagnosis and prognosis methods for cancer diseases. The identification and analysis of proteins associated with disease is a major challenge. Although several biomarkers for tumor diseases such as the prostate specific antigen (PSA), the carcinoembryonic antigen (CEA) or the alpha-fetoprotein (AFP) have been identified and introduced successfully into clinical practice, their sensitivity and specificity have been limited. A good example is prostate cancer, the most frequently diagnosed cancer and the second leading cause of cancer death in men in Western countries. The prostate marker PSA is quite sensitive, however, it does not correctly differentiate benign from malignant prostate disease, and can miss some significant prostate cancers. Therefore, further effort is warranted to search for additional biomarkers in order to improve cancer specificity. It is likely multiple biomarkers will be required to improve early detection, diagnosis and prognosis.

The classical technique for discovering disease-associated proteins is two-dimensional polyacrylamide gel electrophoresis (2D-PAGE) followed by the detection and identification of multiple protein species by matrix-assisted laser desorption ionization time of flight mass spectrometry[1] (MALDI-TOF-MS). This technique is unchallenged in its ability to resolve thousands of proteins but it is laborious, requires large quantities of protein, lacks critical reproducibility, lacks standards and it is not easy to convert the results into a routinely used diagnostic test. Therefore more timesaving and robust techniques are needed. One technique is the ProteinChip approach produced by Ciphergen Biosystems Inc. (Fremont, Calif.). This method uses surface enhanced laser desorption/ionization (SELDI) TOF-MS to detect proteins affinity-bound to a protein chip array. There have been many examples of the use of SELDI for the determination of disease biomarkers, with the primary focus being diagnostics for all forms of cancer. Compared to conventional MS-applications, the SELDI-technology is much easier and timesaving regarding sample preparation and analysis. Other well established profiling techniques are based on different functionalized magnetic-particles and MALDI-TOF-MS and on the direct MALDI-TOF analysis of tissue sections.

[1]MALDI instrumentation and methods are described in references Fenn et al. Science, 246, 64, 1989, Karas et al. Anal. Chem., 60, 2299, 1995, Loo et al. Bioconjugate Chem., 6, 644, 1995, Chaurand et al. J. Am. Soc. Mass. Sectrom. 10, 91, 1999 and Loo et al. Anal. Chem. 65, 425, 1993.

In addition to those MS-based proteomics approaches we recently reported the development and optimization of material enhanced laser desorption ionization (MELDI) by introducing derivatized cellulose, silica beads and other extraction materials for the selective serum-protein profiling with a high-resolution MALDI-TOF MS instrument (Feuerstein et al., J. Proteome Res. 4:2320-2326). For derivatization, glycidyl methacrylate (GMA) was grafted onto 8 μm cellulose beads. In a second step iminodiacetic acid (IDA) was added to the cellulose beads through the epoxide of GMA. The functionalized beads were loaded with copper ions and mixed with serum samples in an Eppendorf tube. After binding of specific proteins (e.g. histidine, tryptophan, or cysteine containing proteins) from a sample, unbound proteins were washed and removed. Next, a small volume (e.g. 1 μl) of the protein-cellulose slurry was directly applied onto a MALDI-target, mixed with sinapinic acid (SA) and directly analyzed with MALDI TOF MS. All of these steps were performed manually.

Here, we describe the automation of the above-described MELDI approach including sample preparation and spotting using small extraction columns and a modified automated liquid handling system such as the MEA Personal Purification System™, commercially available from Phynexus, Inc. (San Jose, Calif.). Using this system, the automated method minimizes the analytical variance introduced by the human handling of samples and increases the robustness of the method.

DESCRIPTION OF SPECIFIC EMBODIMENTS OF THE INVENTION

Figure 1:
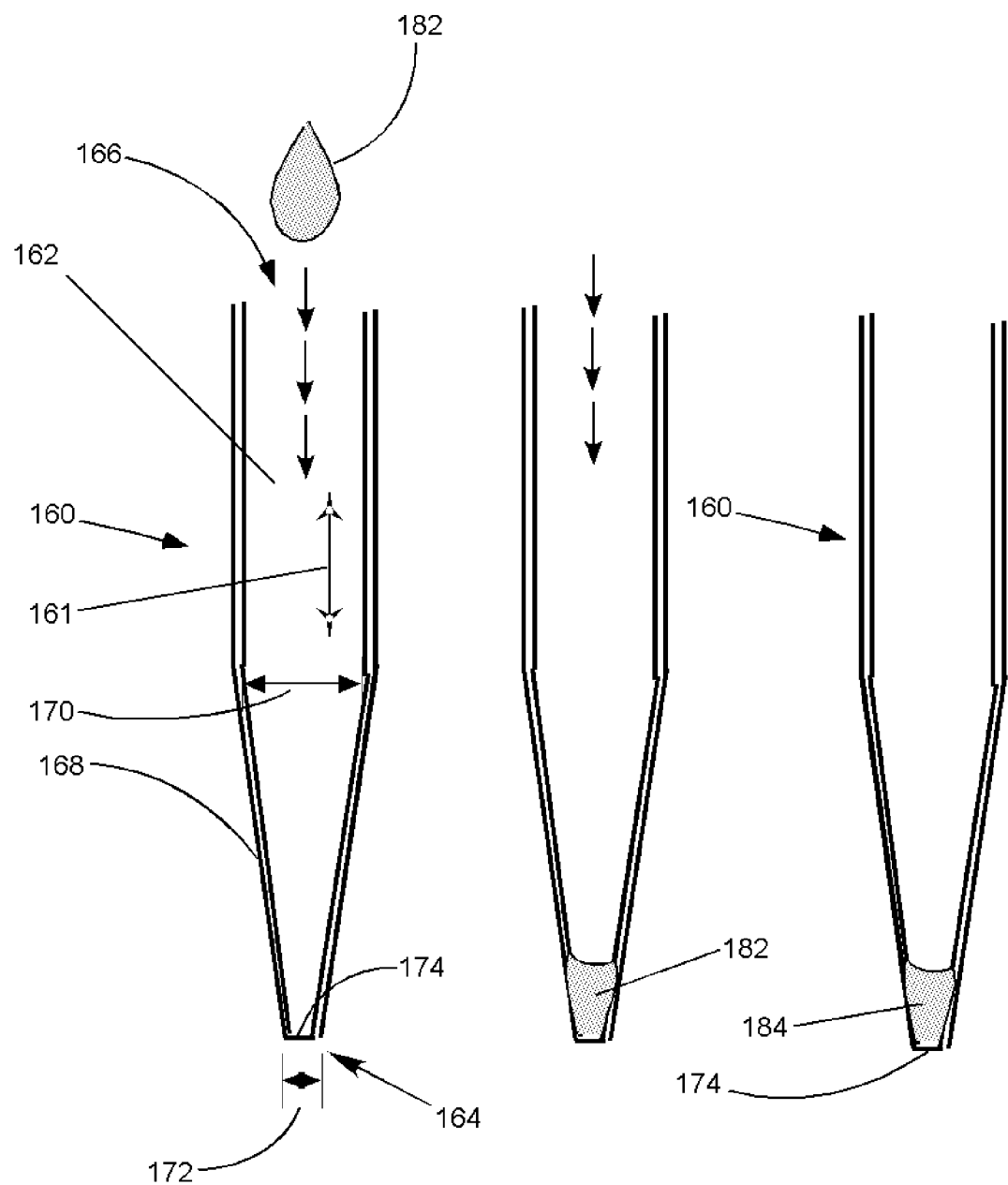
FIG. 1 depicts an embodiment of the invention where the column can take the form of a pipette tip with a screen frit at the bottom of the column bed chamber.

The devices and methods of this invention are useful in the biological sciences, and particularly useful in the "omics" areas such as viromics, transcriptomics, toxicomics, toxicogenomics, toxicoproteomics, tissueomics, steroidomics, secretomics, saccharomics, ribonomics, RNomics, proteomics, peptidomics, oncomics, oncoproteomics, nucleomics, mitochondriomics, metabonomics, metabolomics, lipoproteomics, lipidomics, interacdomics, immunolomics, glycomics, genomics, diseaseomics, diagnomics, cytokinomics and cytomics. The invention relates to methods and devices for extracting an analyte or group of analytes from a sample and analysis with analytical technologies employing MALDI mass spectrometry. The analytes can include biomolecules, particularly biological macromolecules such as proteins, peptides, polynucleotides, carbohydrates, lipids, metabolites, polysaccharides, phosphopeptides, protein complexes, small organic molecules and others. The process generally results in the enrichment, concentration, and/or purification of an analyte or analytes of interest and preparing and spotting the analyte and matrix on a MALDI plate.

In U.S. patent application Ser. No. 10/620,155, incorporated by reference herein in its entirety, methods and devices for performing low dead column extractions are described. The instant specification, inter alia, includes and expands upon the concepts described in that application.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like. Although any methods and materials similar or equivalent to those described herein can be used in the practice or testing of the present invention, specific examples of appropriate materials and methods are described herein.

DEFINITIONS

Unless defined otherwise, all technical and scientific terms used herein have the same meaning as commonly understood by one of ordinary skill in the art to which the invention pertains. The following references provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, The Harper Collins Dictionary of Biology (1991). As used herein, the following terms have the meanings ascribed to them unless specified otherwise.

In describing and claiming the present invention, the following terminology will be used in accordance with the definitions set out below.

"Analyte" refers to a component of a sample which is desirably retained and detected. The term can refer to a single component or a set of components in the sample.

"Complex" refers to analytes formed by the union of two or more analytes.

"Adsorb" refers to the detectable binding between binding functionalities of an adsorbent (e.g., a hydrogel material or uniform particles) and an analyte either before or after washing with an eluant (selectivity threshold modifier).

The term "bed volume" as used herein is defined as the volume of a solid support or bed of media in a column.

"Solid support" is defined as the resin, particles or medium contained within the pipette tip column, columns, tubes, tubings, plates or wells of the instant invention. The term solid support is used synonymously herein with the terms resin, particles, medium and extraction media.

The terms "column", "extraction column" and "extraction tip" as used herein are defined as a column device, the column device containing a bed of solid support material or resin, i.e., media.

The term "frit" as used herein is defined as porous material for holding the solid support in place in a column. A media chamber is typically defined by a bottom frit and optionally a top frit positioned in a column. In some embodiments of the invention the frit is a thin, low pore volume, low back-pressure screen, e.g., a membrane screen.

The term "lower column body" as used herein is defined as the column bed and bottom membrane screen of a column.

The term "membrane screen" as used herein is defined as a woven or non-woven fabric or screen for holding the column packing or solid support in place in the column bed, the membranes having sufficient porosity to allow passage of liquids through the column bed.

The term "sample volume", as used herein is defined as the volume of the liquid of the original sample solution from which the analytes are separated or purified.

The term "upper column body", as used herein is defined as the column chamber.

The terms "automated" or "automation" refer to methods or systems of operating or controlling a process by highly automatic means, as by electronic devices, reducing human intervention to a minimum.

A "liquid handler" or a "liquid handling" system, robot or device is defined herein as a machine which automatically dispenses a selected quantity of a liquid reagent.

The terms "dispense" and "expel" are used synonymously herein.

The term "MALDI matrix" as used herein is a substance that absorbs laser light causing a small part of the target substrate to vaporize for MALDI-TOF MS analysis.

The term "MALDI target" or "MALDI spotting plate" refers to the MALDI plate on which the sample is spotted. The MALDI target is inserted into the MALDI MS for MALDI analysis.

The term "spotting" refers to the placement, transfer or deposition of a solution or slurry onto the MALDI target.

The term "Mass internal standard" as used herein is a protein used for normalization of signal intensity across multiple samples or sample preparations, The term "slurry" is defined herein as a suspension of insoluble particles.

The term "slurry solvent" refers to the solvent used to make the slurry.

An "alignment fixture" is used to properly align and position reagents (e.g. slurry or MALDI matrix) for transfer onto the MALDI target.

A "spotting device" is defined as the alignment fixture in combination with a MALDI target and a pipette tip (or pipette tip column) containing a slurry positioned within the alignment fixture and above the MALDI target.

The term "parallel" or "parallel processing" refers to the simultaneous performance of multiple operations.

"Capture" is defined as bound or associated. A captured analyte in an analyte bound or associated with a solid support.

"Biological sample" refers to a sample derived from a virus, cell, tissue, organ or organism including, without limitation, cell, tissue or organ lysates or homogenates, or body fluid samples, such as blood, urine or cerebrospinal fluid.

The term "biomolecule" as used herein refers to molecules derived from or used with a biological system. The term includes biological macromolecules, such as a proteins, peptides, carbohydrates, metabolites, polysaccharides, nucleic acids and small organic molecules.

"Biopolymer" refers to a polymer or an oligomer of biological origin, e.g., polypeptides or oligopeptides, polynucleotides or oligonucleotides, polysaccharides or oligosaccharides, polyglycerides or oligoglycerides.

"Small organic molecule" refers to organic molecules of a size comparable to those organic molecules generally used in pharmaceuticals or biological systems.

"Resolve," "resolution," or "resolution of analyte" refers to the detection of at least one analyte in a sample. Resolution includes the detection of a plurality of analytes in a sample by separation and/or subsequent differential detection. Resolution does not require the complete separation of an analyte from all other analytes in a mixture. Rather, any separation that allows the distinction between at least two analytes suffices.

"Detect" refers to identifying the presence, absence or amount of the object to be detected. "Organic biomolecule" refers to an organic molecule of biological origin, e.g., steroids, amino acids, nucleotides, sugars, polypeptides, polynucleotides, complex carbohydrates or lipids.

Columns

In accordance with the present invention there may be employed conventional chemistry, biological and analytical techniques within the skill of the art. Such techniques are explained fully in the literature. See, e.g. *Chromatography*, 5$^{th}$ edition, PART A: FUNDAMENTALS AND TECHNIQUES, editor: E. Heftmann, Elsevier Science Publishing Company, New York (1992); ADVANCED CHROMATOGRAPHIC AND ELECTROMIGRATION METHODS IN BIOSCIENCES, editor: Z. Deyl, Elsevier Science BV, Amsterdam, The Netherlands, (1998); CHROMATOGRAPHY TODAY, Colin F. Poole and Salwa K. Poole, and Elsevier Science Publishing Company, New York, (1991).

In some embodiments of the subject invention a solid support is contained in a column, e.g., a low dead volume column. Pipette tip columns used with the MEA Personal Purification System™ (PhyNexus, Inc., San Jose) are well suited for use with the instant invention; however other suitable columns and liquid handling systems can be used. It is to be understood that the subject invention is not to be construed as limited to the use of a solid support in columns. For example, the invention is equally applicable for use with a solid support as a component of a multi-well plate or tubes. In some embodiments, a MALDI matrix can be taken from a deep well plate or tubes and automation can be used to the form a slurry with the column solid support and spot the mixture onto a MALDI target.

In its preferred form, the column is configured to allow processing of the sample and then after processing allow access to the solid support containing the captured analyte so that a slurry can be prepared and deposited on the target. The column can be configured in different ways. In one embodiment, access to the solid support in the column is from the top of the bed.

Column Body

The column body is a tubing having two open ends connected by an open channel, sometimes referred to as a through passageway. The tubing can be in any shape, including but not limited to cylindrical or frustoconical, and of any dimensions consistent with the function of the column as described herein. In some embodiments of the invention the column body takes the form of a pipette tip, however the column body may also take the form of a syringe, a well on a multi-well filter plate or similar tubular bodies. In embodiments where the column body is a pipette tip, the end of the tip wherein the solid support is placed can take any of a number of geometries, e.g., it can be tapered or cylindrical. In some cases a cylindrical channel of relatively constant radius can be used instead of a tapered tip, for a variety of reason, e.g., solution flows through the bed at a uniform rate, rather than varying as a function of a variable channel diameter.

In some embodiments, one of the open ends of the column, sometimes referred to herein as the open upper end of the column, is adapted for attachment to a pump, either directly or indirectly. In some embodiments of the invention the upper open end is operatively attached to a pump, whereby the pump can be used for aspirating (i.e., drawing) a fluid into the column through the open lower end of the column, and optionally for discharging (i.e., expelling) fluid out through the open lower end of the column. Thus, it is a feature certain embodiments of the present invention that fluid enters and exits the column through the same open end of the column, typically the open lower end. In other embodiments, fluid enters the column through one open end and exits through the other end after traveling through the solid support, i.e., similar to conventional column chromatography. The fluid can be a liquid, such as a sample solution, wash solution or slurry solvent. The fluid can also be a gas, e.g., air used to blow liquid out of the column.

Various plastics make ideal column body materials, but other materials such as glass, ceramics or metals could be used in some embodiments of the invention. Some examples of column body materials include polysulfone, polypropylene, polyethylene, polyethyleneterephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials.

The volume of the column body is typically in the range of at least 1 ul to at most 20 ml. In those embodiments where the column body takes the form of a pipette tip, typical volumes are 10 ul, 20 ul, 200 ul, 250 ul, 1000 ul and 5000 ul. Some specific examples of suitable column bodies are provided in the Examples section.

Column Solid Support

The solid support used in the column is preferably a form of water-insoluble particle (e.g., a porous or non-porous bead, monolith, particle or fiber) that has an affinity or attraction for an analyte of interest. Column solid supports may also be referred to herein using the terms media, extraction media, resins particles, and beads. The term analyte as used herein can refer to any compound of interest, e.g., to be analyzed, or to a heterogeneous collection of biomolecules. Typical biomolecules include proteins, peptides, nucleic acids, lipids, carbohydrates, small organic molecules and metabolites; however the analyte can be any biomolecule. Sources of biomolecules can be eukaryotic or prokaryotic and can include biological samples such as serum, urine, stool, cell, body fluid or excretion samples, tissue, organ, organ lysate or homogenate, blood, saliva, spinal fluid, cerebrospinal fluid, tissue culture, cell culture, bacteria, yeast, virus, etc.

The preparation processes can be affinity, size exclusion, reverse phase, normal phase, ion exchange, hydrophobic interaction chromatography, or hydrophilic interaction chromatography agents. In general, the term "solid support" is used in a broad sense to encompass any media capable of effecting separation, either partial or complete, of an analyte from another. The term "analyte" can refer to any compound or group of compounds of interest, e.g., to be analyzed or simply removed from a solution.

The volume of the solid support used in the columns of the invention is typically 200 µL or less although it can be more. Typical ranges include 0.01 µL-200 µL, usually in the range of 0.1 µL-10 µL. The low bed volumes employed in certain embodiments contribute to a low interstitial volume of the bed, reducing the dead volume of the column. The low bed volumes employed in certain embodiments allow for the use of relatively small amounts of solid support. For example, some embodiments of the invention employ a solid support having a dry weight of 1 gram or less (e.g., in the range of 0.001 mg-1 g).

Many solid supports suitable for use in the invention are selected from a variety of classes of chromatography media. It has been found that many of these chromatography media and their associated chemistries are suited for use as a solid support in the devices and methods of this invention.

Thus, examples of suitable solid supports include resin beads used for preparation and/or chromatography. Examples of useful resins include gel resins, pellicular resins, microporous resins, fibrous resins, molecular sieve resins and macroporous resins.

The term "macroporous resin" refers to highly crosslinked resins having high surface area due to a physical porous structure that formed during the polymerization process. Macroporous resins behave similar to pellicular resins except that in effect much more surface area is available for interaction of analyte with resin functional groups.

The term "pellicular resins" refers to materials in which the functional groups are on the surface of the bead or in a thin layer on the surface of the bead. The interior of the bead is solid, usually highly crosslinked, and usually inaccessible to the solvent and analytes. Pellicular resins generally have lower capacities than gel and macroporous resins.

Gel resins can be non-porous or micro-porous beads. The term "gel resin" refers to a resin comprising low-crosslinked bead materials that can swell in a solvent, e.g., upon hydration. Crosslinking refers to the physical linking of the polymer chains that form the beads. The physical linking is normally accomplished through a crosslinking monomer that contains bi-polymerizing functionality so that during the polymerization process, the molecule can be incorporated into two different polymer chains. Cellulose fiber and soft gel resin beads, such as agarose and sepharose based beads, are found to work well in columns and methods of this invention. Non-limiting examples of gel resins include agarose, sepharose, polystyrene, polyacrylate, cellulose, silica, diamond, glycidyl methacrylate (GMA) copolymerized with divinylbenzene (DVB), polystyrene/divinylbenzene copolymers, poly methylmethacrylate, protein G beads (e.g., for IgG protein purification), MEP Hypercel™ beads (e.g., for IgG protein purification), affinity phase beads (e.g., for protein purification), ion exchange phase beads (e.g., for protein purification), hydrophobic interaction beads (e.g., for protein purification), reverse phase beads (e.g., for nucleic acid or protein purification), and beads having an affinity for molecules analyzed by label-free detection and others. In some embodiments, the solid support is comprised of a mixture of two or more materials. In one embodiment the solid support is comprised of a library such as a library of beads having a variety of ligands.

The support can be derivatized with iminodiacetic acid, nitrilotriacetic acid, N-Carboxy-β-Alanin, Aspartic acid, 2-Amino-2-Methyl-Propandi-Acid, 2-Furanacetic acid, 5-Ethyl-3-Hydroxy-4-Methyl-2(5H)-Furanon, Tetrahydro-4-Methylen-3-Furanacetic acid, 2-Butendi-acid, 2-Butendi-acid, Methylen-Propandi-acid and others as well as mixtures of the above. In case of chelators, particles can be loaded with Copper, Iron, Gallium, Cobalt, Aluminum, Zinc, Manganese, Nickel, diamond, nanotubes, affinity groups, ion exchange groups and others.

The average particle diameters of beads of the invention are typically in the range of about 1 µm to several millimeters, e.g., diameters in ranges having lower limits of 1 µm, 5 µm, 10 µm, 20 µm, 30 µm, 40 µm, 50 µm, 60 µm, 70 µm, 80 µm, 90 µm, 100 µm, 150 µm, 200 µm, 300 µm, or 500 µm, and upper limits of 10 µm, 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm. In certain embodiments the particle diameter is in the range of 20 µm to 100 µm.

The bead size that may be used depends somewhat on the bed volume and the cross sectional area of the column. A lower bed volume column will tolerate a smaller bead size without generating the high backpressures that could burst or plug a thin membrane frit. For example a bed volume of 0.1 to 1 µL, can tolerate 5 to 10 µm particles. Larger beds (up to about 50 µL) normally have bead sizes of 30-150 µm or higher. The upper range of particle size is dependant on the diameter of the column bed. The bead diameter size should not be more than 50% of the bed diameter, and it is usually less than 10% of the bed diameter. The bead diameter also depends on the performance of the deposited material or a MALDI target. Smaller beads can give more consistent or reproducible mass spectral data.

The chemistry employed in the present invention can take any of a wide variety of forms. For example, the solid support can be selected from, or based on, any of the chemistries used in solid-phase extraction and/or chromatography, e.g., reverse-phase, normal phase, hydrophobic interaction, hydrophilic interaction, ion-exchange, thiophilic separation, hydrophobic charge induction, molecular sieve adsorption or affinity binding. Because the invention is particularly suited to the purification and/or concentration of biomolecules, surfaces capable of adsorbing such molecules are particularly relevant. See, e.g., SEPARATION AND SCIENCE TECHNOLOGY Vol. 2.: HANDBOOK OF BIOSEPARATIONS, edited by Satinder Ahuja, Academic Press (2000).

Affinity extractions or preparations use a technique in which a bio-specific adsorbent is prepared by coupling a specific ligand (such as an enzyme, antigen, or hormone) for the analyte, (e.g., macromolecule) of interest to a solid support. This immobilized ligand will interact selectively with molecules that can bind to it. Molecules that will not bind elute unretained. The interaction is selective and reversible. The references listed below show examples of the types of affinity groups that can be employed in the practice of this invention are hereby incorporated by reference herein in their entireties. Antibody Purification Handbook, *Amersham Biosciences*, Edition AB, 18-1037-46 (2002); Protein Purification Handbook, *Amersham Biosciences*, Edition AC, 18-1132-29 (2001); Affinity Chromatography Principles and Methods, *Amersham Pharmacia Biotech*, Edition AC, 18-1022-29 (2001); The Recombinant Protein Handbook, *Amersham Pharmacia Biotech*, Edition AB, 18-1142-75 (2002); and *Protein Purification: Principles, High Resolution Methods, and Applications*, Jan-Christen Janson (Editor), Lars G. Ryden (Editor), Wiley, John & Sons, Incorporated (1989).

Examples of suitable affinity binding agents include those from one or more of the following interaction categories:
1. Chelating metal—ligand interaction
2. Protein—Protein interaction
3. Organic molecule or moiety—Protein interaction
4. Sugar—Protein interaction
5. Nucleic acid—Protein interaction
6. Nucleic acid—nucleic acid interaction In one aspect of the invention a medium is used that contains a surface functionality that has an affinity for a protein fusion tag used for the purification of recombinant proteins. A wide variety of fusion tags and corresponding affinity groups are available and can be used in the practice of the invention.

U.S. patent application Ser. No. 10/620,155 describes in detail the use of specific affinity binding reagents in solid-phase extraction. Examples of specific affinity binding agents include proteins having an affinity for antibodies, Fc regions and/or Fab regions such as Protein G, Protein A, Protein A/G, and Protein L; chelated metals such as metal-NTA chelate (e.g., Nickel NTA, Copper NTA, Iron NTA, Cobalt NTA, Zinc NTA), metal-IDA chelate (e.g., Nickel IDA, Copper IDA, Iron IDA, Cobalt IDA) and metal-CMA (carboxymethylated aspartate) chelate (e.g., Nickel CMA, Copper CMA, Iron CMA, Cobalt CMA, Zinc CMA); glutathione surfaces-nucleotides, oligonucleotides, polynucleotides and their analogs (e.g., ATP); lectin surface-heparin surface-avidin or streptavidin surface, a peptide or peptide analog (e.g., that binds to a protease or other enzyme that acts upon polypeptides). Examples of methods for particle preparation and derivatization are described in Examples 9 through 12.

In some embodiments of the invention, the affinity binding reagent is one that recognizes one or more of the many affinity groups used as affinity tags in recombinant fusion proteins. Examples of such tags include poly-histidine tags (e.g., the 6×-His tag), which can be extracted using a chelated metal such as Ni-NTA-peptide sequences (such as the FLAG epitope) that are recognized by an immobilized antibody; biotin, which can be extracted using immobilized avidin or streptavidin; "calmodulin binding peptide" (or, CBP), recognized by calmodulin charged with calcium-glutathione S-transferase protein (GST), recognized by immobilized glutathione; maltose binding protein (MBP), recognized by amylose; the cellulose-binding domain tag, recognized by immobilized cellulose; a peptide with specific affinity for S-protein (derived from ribonuclease A); and the peptide sequence tag CCxxCC (where xx is any amino acid, such as RE), which binds to the affinity binding agent bis-arsenical fluorescein (FlAsH dye).

Antibodies can be extracted using, for example, proteins such as protein A, protein G, protein L, hybrids of these, or by other antibodies (e.g., an anti-IgE for purifying IgE).

Chelated metals are not only useful for purifying poly-his tagged proteins, but also other non-tagged proteins that have an intrinsic affinity for the chelated metal, e.g., phosphopeptides and phosphoproteins. Non-limiting examples of useful chelating metals include iron, copper, aluminum, manganese, cobalt, zinc, gallium, and nickel.

Antibodies can also be useful for purifying non-tagged proteins to which they have an affinity, e.g., by using antibodies with affinity for a specific phosphorylation site or phosphorylated amino acids.

In other embodiments of the invention solid support materials are employed that are generally less specific than the affinity binding agents discussed above. These chemistries are still often quite useful. Examples include ion exchange, reversed phase, normal phase, molecular sieve, hydrophobic interaction and hydrophilic interaction extraction or chromatography surfaces. In general, these chemistries, methods of their use, appropriate solvents, etc. are well known in the art, and in particular are described in more detail in U.S. patent application Ser. Nos. 10/434,713 and 10/620,155, and references cited therein, e.g., Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 3 94 (1991); and ORGANIC SYNTHESIS ON SOLID PHASE, F. Dorwald Wiley VCH Verlag Gmbh, Weinheim 2002.

Frits

In some embodiments of the invention one or more frits are used to contain the solid support in, for example, a column. Frits can take a variety of forms, and can be constructed from a variety of materials, e.g., glass, ceramic, metal, fiber. Some embodiments of the invention employ frits having a low pore volume, which contributes to reducing dead volume. The frits of the invention are porous, since it is necessary for fluid to be able to pass through the frit. The frit should have sufficient structural strength so that frit integrity can contain the solid support in the column. It is desirable that the frit have little or no affinity for chemicals with which it will come into contact during the preparation process, particularly the analyte of interest. In many embodiments of the invention the analyte of interest is a biomolecule, particularly a biological macromolecule. Thus in many embodiments of the invention it desirable to use a frit that has a minimal tendency to bind or otherwise interact with biological macromolecules, particularly proteins, peptides, phosphopeptides and nucleic acids.

Frits of various pores sizes and pore densities may be used provided the free flow of liquid is possible and the beads are held in place within the solid support.

In one embodiment, one frit (e.g., a lower frit) is bonded to and extends across the open channel of the column body.

Frits of the invention can have pore openings or mesh openings of a size in the range of about 5-200 µm, often in the range of 10-100 µm, and usually 15-50 µm, e.g., about 43 µm. The performance of the column is typically enhanced by the use of frits having pore or mesh openings sufficiently large so as to minimize the resistance to flow. The use of membrane screens as described herein typically provide this low resistance to flow and hence better flow rates, reduced back pressure and minimal distortion of the solid support. The pore or mesh openings of course should not be so large that they are unable to adequately contain the solid support in the chamber.

The frits of the invention, e.g., a membrane screen, can be made from any material that has the required physical properties as described herein. Examples of suitable materials include nylon, polyester, polyamide, polycarbonate, cellulose, polyethylene, nitrocellulose, cellulose acetate, polyvinylidine difluoride, polytetrafluoroethylene (PTFE), polypropylene, polysulfone, metal and glass. A specific example of a membrane screen is the 43 µm pore size Spectra/Mesh® polyester mesh material which is available from Spectrum Labs (Ranch Dominguez, Calif., PN 145837).

Column Assembly

The columns of the invention can be constructed by a variety of methods using the teaching supplied herein.

In some embodiments, the column body is a tubular member, particularly pipette tips, sections of pipette tips or modified forms of pipette tips.

FIG. 1 illustrates the construction of an example of an embodiment of the columns of the invention. This example includes a column body 160 having a longitudinal axis 161, a central through passageway 162 (i.e., an open channel), an open lower end 164 for the uptake and/or expulsion of fluid, and an open upper end 166 for operable attachment to a pump, e.g., the open upper end is in communication with a pipettor, multi-channel pipettor, or an automated liquid handling system. The communication can be direct or indirect, e.g., through one or more fittings, couplings or the like, so long as operation of the pump effects the pressure in the central through passageway. The column body includes a frustoconical section 168 of the through passageway 162, which is adjacent to the open lower end 164. The inner diameter of the frustoconical section decreases from a first inner diameter 170, at a position in the frustoconical section distal to the open lower end, to a second inner diameter 172 at the open lower end. A lower frit 174, which can be a membrane screen, is bonded to and extends across the open lower end 164. In one embodiment a membrane frit can be bound to the column body by methods described herein, such as by gluing or welding. To construct the column, a desired quantity of solid support 182, usually in the form of a slurry, is introduced into the through passageway through the open upper end and positioned in the frustoconical section adjacent to the open lower end. The solid support forms a packed bed in contact with the lower frit 174. The lower frit, and the surface of the through passageway bounded by the media bed define a media chamber 184. The amount of solid support introduced into the column is normally selected such that the solid support partially fills the media chamber.

In some embodiments, an upper frit may be used. Embodiments that utilize an upper frit are described in more detail in U.S. patent application Ser. No. 10/620,155 which is incorporated in its entirety herein. If desired, one could attach frits by pressure, bonding, gluing, welding, etc. In some embodiments, frits may be attached by grooves, locking mechanisms, etc.

In the foregoing embodiments, the ring and latitudinal cross sections of the frustoconical section are illustrated as circular in geometry. Alternatively, other geometries could be employed, e.g., oval, polygonal or otherwise. Whatever the geometries, the frit and frustoconical shapes should match to the extent required to achieve and adequately sealing engagement. The frits are usually, bit not necessarily, positioned in a parallel orientation with respect to one another and perpendicular to the longitudinal axis.

Other embodiments of the invention exemplifying different methods of construction are also described in U.S. patent application Ser. No. 10/620,155.

Solid Supports and Solvents

Column preparation of analytes for MALDI-TOF MS typically involves loading the column with a sample solution containing the analytes and rinsing the column with a wash solution. With regard to the sample solution, it typically consists of the analyte dissolved in a solvent in which the analyte is soluble, and in which the analyte will bind to the solid support. Preferably, the binding is strong, resulting in the binding of a substantial portion of the analyte, and optimally substantially all of the analyte will be bound under the loading protocol used in the procedure.

The analyte should be in a solvent compatible with spotting on the MALDI target and with the MALDI matrix employed. The capture, wash and slurry solvents are chosen to be compatible with the analyte and the detection method. A wash solution, if used, should be selected such that it will remove non-desired contaminants with minimal loss or damage to the bound analyte. Generally, the solvents used are known conventional solvents. Typical slurry solvents from which a suitable solvent can be selected include methylene chloride, acetonitrile (with or without small amounts of basic or acidic modifiers), methanol (containing larger amount of modifier, e.g. acetic acid or triethylamine, or mixtures of water with either methanol or acetonitrile), ethyl acetate, chloroform, hexane, isopropanol, acetone, alkaline buffer, high ionic strength buffer, acidic buffer, strong acids, strong bases, organic mixtures with acids/bases, acidic or basic methanol, tetrahydrofuran and water. In certain embodiments the slurry solvent also contains the MALDI matrix.

In the case where the preparation involves binding of analyte to a specific cognate ligand molecule, e.g., an immobilized metal, the slurry solvent can contain a molecule that will interfere with such binding, e.g., imidazole or low pH.

After loading and optionally washing of the column, a slurry is prepared from the column media. The slurry is spotted onto a MALDI target for mass spectrometer analysis. Examples of suitable phases for solid phase extraction, analyte preparation and slurry solvents are shown in Tables A and B.

TABLE A

|  | Normal Phase Extraction | Reverse Phase Extraction | Reverse Phase Ion-Pair Extraction |
|---|---|---|---|
| Typical solvent polarity range | Low to medium | High to medium | High to medium |
| Typical sample loading solvent | Hexane, toluene, $CH_2Cl_2$ | $H_2O$, buffers | $H_2O$, buffers, ion-pairing reagent |
| Typical slurry solvent | Ethyl acetate, acetone, $CH_3CN$ (Acetone, acetonitrile, isopropanol, methanol, water, buffers) | $H_2O/CH_3OH$, $H_2O/CH_3CN$ (Methanol, chloroform, acidic methanol, basic methanol, tetrahydrofuran, acetonitrile, acetone, ethyl acetate,) | $H_2O/CH_3OH$, ion-pairing reagent $H_2O/CH_3CN$, ion-pairing reagent (Methanol, chloroform, acidic methanol, basic methanol, tetrahydrofuran, acetonitrile, acetone, ethyl acetate) |

TABLE B

|  | Ion Exchange Extraction | Hydrophobic Interaction Extraction | Affinity Phase Extraction |
|---|---|---|---|
| Typical solvent polarity range | High | High | High |
| Typical sample loading solvent | $H_2O$, buffers | $H_2O$, high salt | $H_2O$, buffers |
| Typical slurry solvent | Buffers, salt solutions | $H_2O$, low salt | $H_2O$, buffers, pH, competing reagents, heat, solvent polarity |

Apparatus and Methods for Using the Columns

Although the methods described below frequently refer to a single pipette tip column, or column, it is to be understood that the methods are often performed in parallel. That is, multiple samples are prepared simultaneously. And although the methods often refer to a pipette tip column, it is to be understood that the methods can also be performed in a plate having multiple wells, or in tubes.

Generally the first step in a preparation procedure of the invention will involve introducing a sample solution containing an analyte of interest into a solid support, typically in the form of a column as described earlier. The sample can be conveniently introduced into the solid support by aspirating and dispensing the solution through the column using a liquid handling system. Note that the volume of sample solution can be much larger than the bed volume. The sample solution can optionally be passed through the column more than one time, e.g., by being pumped back and forth through the solid support repeatedly. This can improve adsorption of analyte, which can be particularly useful in cases where the analyte is of low abundance.

Certain embodiments of the invention are particularly suited to the processing of biological samples, where the analyte of interest is a biomolecule. The sample solution can be any solution containing an analyte of interest. The invention is particularly useful for preparation, extraction and purification of biological molecules, hence the sample solution is often of biological origin, e.g., serum or urine. Of particular relevance are biological molecules such as proteins, small organic molecules, phosphopeptides, carbohydrates, metabolites, polypeptides, polynucleotides, and polysaccharides, or large complexes containing one or more of these moieties.

An exemplary pipet tip column of the present invention might have a bed size of 1 mg positioned in right-angle frustum (i.e., an inverted cone with the tip chopped off, where the bottom diameter is 3 mm and the approximate bed height is 8 mm).

Columns of the invention can accommodate a variety of flow rates, and the invention provides methods employing a wide range of flow rates, oftentimes varying at different steps of the method. In some cases, it is desirable to perform one or more steps of a purification process at a relatively slow flow rate, e.g., the loading and/or wash steps, to maximize binding of an analyte of interest to a solid support. To facilitate such methods, in certain embodiments the invention provides a pipette comprising a column body; a microprocessor; an electrically driven actuator disposed within the body, the actuator in communication with and controlled by the microprocessor; a displacement assembly including a displacing piston moveable within one end of a displacement cylinder having a displacement chamber and having another end with an aperture, wherein said displacing piston is connected to and controlled by said actuator; and a pipette tip in communication with said aperture, wherein the microprocessor is programmable to cause movement of the piston in the cylinder at a rate that results in drawing a liquid into the pipette tip at a desired flow when the tip is in communication with the liquid. The flow rate can be relatively slow, such as the slow flow rates described above, e.g., between about 0.1 and 4 mL/min. In some embodiments, the process is controlled by a liquid handling system comprised of a microprocessor in communication with a multichannel pipettor.

The pipette tip can be a pipette tip column of the invention, e.g., a pipette tip comprising a tip body having an open upper end, an open lower end, and an open channel between the upper and lower ends of the tip body; a bottom frit extending across the open channel; optionally a top frit extending across the open channel between the bottom frit and the open upper end of the tip body, wherein the bottom frit, optional top frit and column body define a media chamber; and a solid support positioned inside the media chamber. An example of a suitable pipette tip column is the PhyTip® column (PhyNexus, Inc. San Jose, Calif.).

In some embodiments, the microprocessor is external to the body of the pipettor, e.g., an external PC programmed to control a sample processing procedure. In some embodiments the piston is driven by a motor, e.g., a stepper motor.

The invention provides a pipettor (such as a multi-channel pipettor or liquid handling robot) suitable for acting as the pump in methods such as those described above. In some embodiments the pipettor comprises an electrically driven actuator. The electrically driven actuator can be controlled by a microprocessor, e.g., a programmable microprocessor. In various embodiments the microprocessor can be either internal or external to the pipettor body. In certain embodiments the microprocessor is programmed to pass a pre-selected volume of solution through the solid support at a pre-selected flow rate.

The back pressure of a column will depend on the average bead size, bead size distribution, average bed length, average cross sectional area of the bed, back pressure due to the frit and viscosity of flow rate of the liquid passing through the bed. For a 1 mg bed described in this application, the backpressure at 1 mL/min flow rate ranged from 0.2 to 2 psi. Other column dimensions will result in backpressures ranging from, e.g., 0.1 psi to 30 psi depending on the parameters described above. The average flow rate ranges from 0.05 mL/min to 10 mL/min, but will commonly be 0.1 to 2 mL/min range with 0.2-1 mL/min flow rate being most common for the 10 uL bed columns.

After the sample solution has been introduced into the bed and analyte allowed to adsorb, the sample solution is substantially evacuated from the bed, leaving the bound analyte. It is not necessary that all sample solution be evacuated from the bed, but diligence in removing the solution can improve the purity of the final product. An optional wash step between the adsorption and desorption steps can also improve the purity of the final product. Typically water or a buffer is used for the wash solution. The wash solution is preferably one that will, with a minimal desorption of the analyte of interest, remove excess sample materials, lightly adsorbed or non-specifically adsorbed materials. The wash cycle can include solvent or solvents having a specific pH, or containing components that promote removal of materials that interact lightly with the solid support. In some cases, several wash solvents might be used in succession to remove specific material, e.g., PBS followed by water. These cycles can be repeated as many times as necessary. In other cases, a wash cycle can be omitted.

In some embodiments, the analyte or group of analytes adsorbed to the solid support is deposited directly onto a MALDI target and analyzed by MALDI TOF MS. In these embodiments, a slurry can be produced with the solid support and an organic solvent, such as acetonitrile or trifluoroacetic acid.

In other embodiments, a MALDI matrix is added to the solid support that has adsorbed analytes prior to deposition on the MALDI target. A suitable MALDI matrix should have the following properties: be able to embed and isolate the analyte (e.g., by co-crystallization), be soluble in solvents compatible with the analytes(s), be vacuum stable, adsorb the laser wavelength, cause co-desorption of the analyte upon laser irradiation, and promote analyte ionization. Examples of suitable MALDI matrix materials include Cinnamic acid derivatives such as sinapinic acid (SA), α-cyano-4-hydroxycinnamic acid (HCCA), cyano hydroxy cinnamic acid ("CHCA"), dihydroxybenzoic acid and others. Other suitable energy absorbing molecules are known to those skilled in this art. For example, see U.S. Pat. No. 5,719,060 (Hutchens & Yip) for additional description of energy absorbing molecules.

There must be access to the solid support in order to add the MALDI matrix. In some embodiments of the invention, only a bottom frit is used in the column construction and access to the solid support is gained from the top of the column. In these embodiments, the pipette tip columns are ejected into a holder to allow access to the solid support via a pipette tip entering the top of the column. Then MALDI matrix can be added to the solid support using a pipette tip and a slurry produced by aspirating and dispensing the matrix and the solid support within the tip. It is often advantageous to perform repeated aspiration and dispense steps to thoroughly mix the slurry. The terms "dispense" and "expel" are used synonymously herein.

In certain embodiments the column does not have a top frit and is open or the frit can be pierced. After sample processing a pipette tip containing a liquid enters the column from the top, deposits the liquid and makes a slurry of liquid and solid support by aspirating and expelling the liquid and solid support back and forth.

In some embodiments a mass internal standard is also added to slurry. The mass internal standard allows for internal recalibration and serves as a control for optimal sample preparation. Examples of suitable mass internal standards are angiotensin I, cytochrome C, ubiquitin, insulin, however many different proteins can be used.

After the MALDI matrix and/or mass internal standard is added to the solid support and a slurry is produced, the slurry is drawn up into a pipette tip. The tip is then positioned above the MALDI target using the alignment fixture and a drop of slurry is deposited onto a MALDI target.

The slurry may be prepared in the column or alternatively, the solid support may be removed or blown out from the column into a plate or well and the slurry prepared there.

In some embodiments a MALDI matrix material is added prior to slurry preparation.

In certain embodiments, both a MALDI matrix material and a mass internal standard are added to the solid support prior to slurry preparation. When the analyte is prepared in a pipette tip column, the MALDI matrix and mass internal standard can be added through the open upper end of the column.

Figure 6:
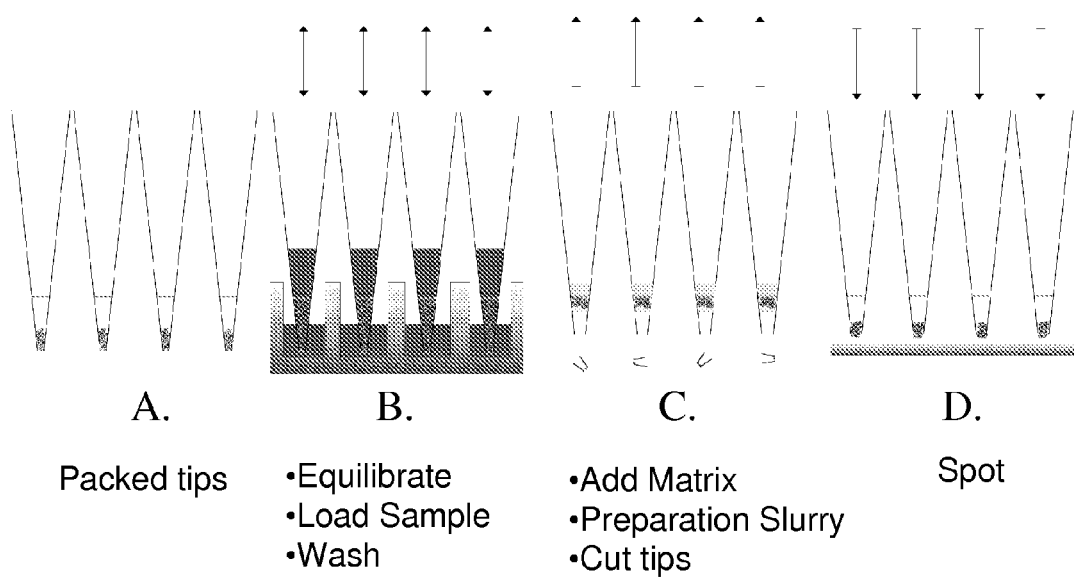
FIG. 6 is a schematic diagram of the MELDI preparation process using a pipette tip column.
Figure 8:
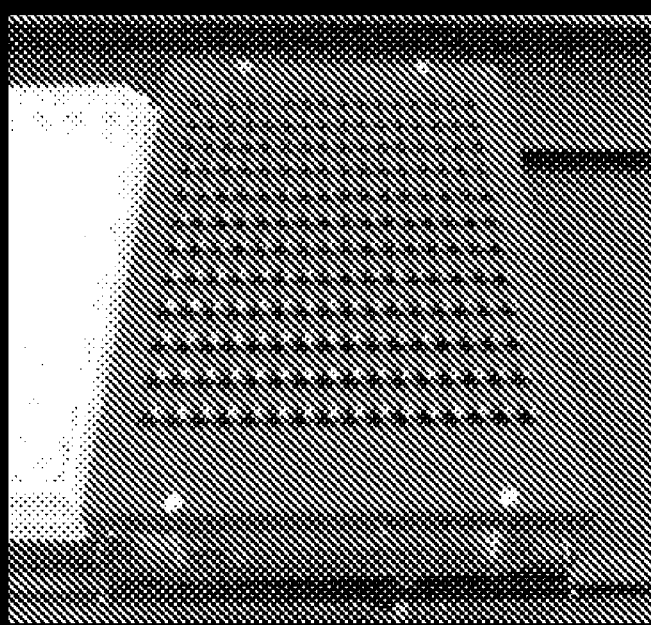
FIG. 8A is a photograph of the MEDLI alignment fixture seated above a MALDI target and 8B is a spotted MALDI target.
Figure 8:
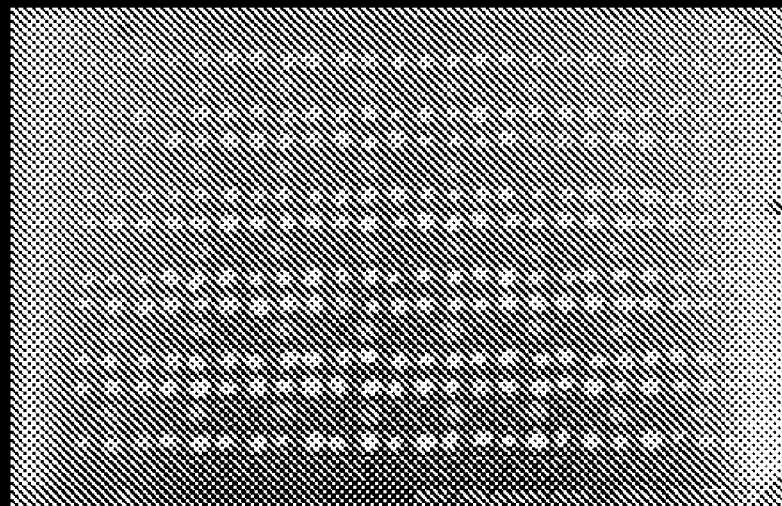

In one embodiment, the slurry is removed from the open upper end of a pipette column and transferred to the MALDI target (following the step B in FIG. 6). In other embodiments the column bottom is cut as exemplified in FIG. 6C and the slurry containing the solid support, analyte and optionally MALDI matrix and/or mass internal standard is pushed through the end of the column and spotted onto a MALDI target (FIG. 8). Alternatively, the frit can be cut away or pierced. Access to the top of the column can also be gained by piercing or cutting away a top frit (when present).

In one embodiment a spotting device is used to deposit the slurry on the MALDI target. A "spotting device" is defined as the alignment fixture in combination with a MALDI target and a pipette tip containing a slurry positioned within the alignment fixture and above the MALDI target. In certain embodiments the tips are pipette tip columns. The alignment and positioning process can be important often the tips or columns can be non uniform or curved. The position where the slurry is to be deposited on the MALDI target is precisely defined so that automatic analysis of the spot can be performed by the mass spectrometer. If the slurry spot is not in the correct or defined position on the MALDI target, automatic analysis of the target may not be possible. Positioning of the tips using the alignment fixture and a liquid handling system can be done in 3 dimensions if necessary including the distance of the lower end of the pipette tip or pipette tip column above the MALDI target. In certain embodiments the lower end of the tip is positioned in the range of 0.03-3 mm above the target. In some embodiments the end of the tips is positioned in the range of 0.1-2 mm above the target.

Figure 7:
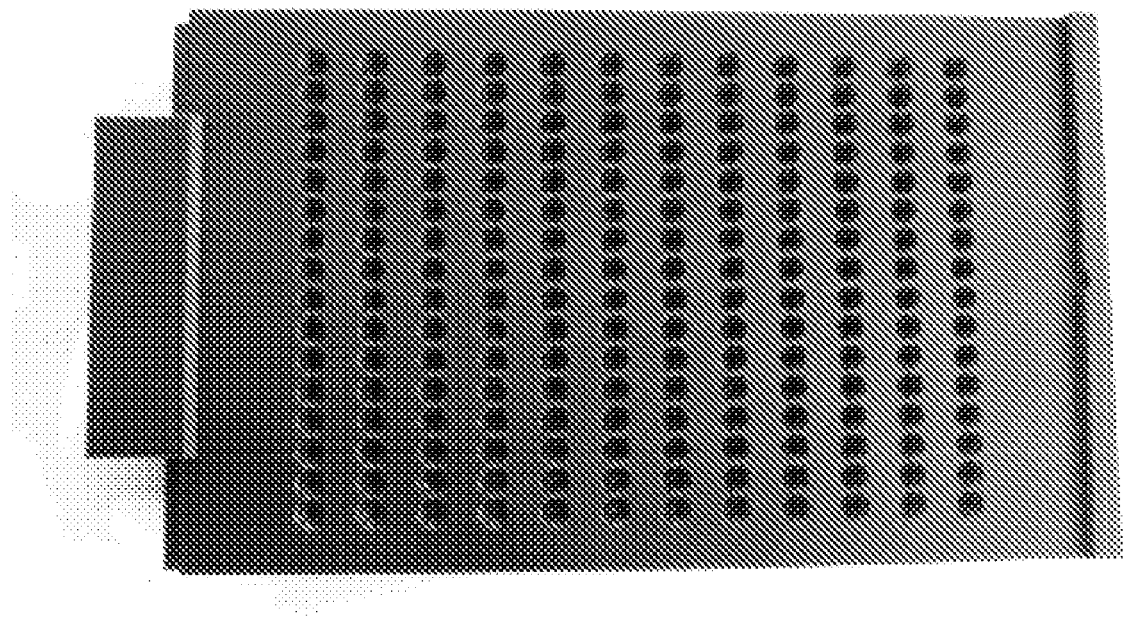
FIG. 7 is a top down photograph of the MEDLI alignment fixture.

The MELDI spotting alignment fixture (FIG. 7) is used to align and position the pipette tips containing the slurry to the appropriate position above the target to deposit the slurry. The alignment fixture is a device that has a system of holes or guides that can accept and position one or more tips or columns over a MALDI target plate. In the example of the spotting alignment fixture shown in this figure, a MALDI target that contains 384 positions (Bruker, Billerica, Mass.) lies underneath the spotting alignment fixture. Spotting is done 12 at a time until 16 rows are completed making a total of 192 spots. Then the alignment fixture is shifted 4.5 mm so that another 192 spots can be made making a total of 384 spots. Once the slurries have been spotted, the plate is dried and placed in the MALDI mass spectrometer.

Depending on the mass spectrometer (MS) used, the alignment fixture can be configured to accept different MALDI targets. An Agilent (Santa Clara, Calif.) MALDI target contains 96 places for accepting slurry in a 12 by 8 spacing format with 4.5 mm spacing. Two of these targets can be positioned in the left side of the spotting alignment fixture so that 24 by 8 spacing can be configured to accept slurry. The same procedure is used for spotting slurry as was performed with the Bruker MALDI target except 96 positions are spotted, the two targets are shifted 4.5 mm and then the other 96 positions are spotted. Other MS manufacturers include ABI and Waters.

In alternate embodiments, spotting can be accomplished using a pin. For example, archived samples stored in a 96-well plate can be spotted onto a MALDI target manually (or in automated fashion) using a 96-well pin tool.

The volume of slurry solvent used can be very small, approximating the interstitial volume of the solid support. Alternatively, the volume of slurry solvent used can be quantified in terms of percent of solid support volume (i.e., the total volume of the solid support plus interstitial space) rather than percent of interstitial volume. For example, ranges of slurry solvent volumes appropriate for use with the invention can be 1×-10,000× the solid support volume, 20 to 100% of the solid support volume 10 to 50%, 100 to 500%, 200 to 5000%, etc., of the solid support volume.

In some embodiments of the invention, the amount of slurry solvent introduced into the column is less than 200 μL, less than 100 μL, less than 20 μL, less than 15 μL, less than 10 μL, less than 5 μL, or less than 1 uL. For example, ranges of desorption solvent volumes appropriate for use with the invention can have a lower limit of 0.1 µL, 0.2 µL, 0.3 µL, 0.5 µL, 1 µL, 2 µL, 3 µL, 5 µL, or 10 µL, and an upper limit of 2 µL, 3 µL, 5 µL, 10 µL, 15 µL, 20 µL, 30 µL, 50 µL, or 100 µL, e.g., in between 1 and 15 µL, 0.1 and 10 µL, or 0.1 and 2 µL.

The slurry solvent may vary depending upon the nature of the analyte and solid support. For example, where the analyte is a His-tagged protein and the solid support is an IMAC resin, the slurry solvent may contain imidazole or the like to release the protein from the solid support. In some cases desorption is achieved by a change in pH or ionic strength, e.g., by using low pH or high ionic strength desorption solution. A suitable slurry solution can be arrived at using available knowledge by one of skill in the art.

Columns and devices of the invention should be stored under conditions that preserve the integrity of the solid support. For example, columns containing agarose- or sepharose-based supports should be stored under cold conditions (e.g., 4 degrees Celsius) and in the presence of 0.01 percent sodium azide or 20 percent ethanol. Prior to using the column, a conditioning step may be employed. This step is to ensure that the column is in a uniform ready condition, and can involve treating with a solvent and/or removing excess liquid from the solid support. If agarose or similar gel materials are used, the solid support should be kept fully hydrated before use.

In certain embodiments, it is desirable to archive or store the solid support with bound analytes for a period of time. The period of time could be on the order of hours, days, week, months or even years. Storage can take place in the columns, or analytes bound to the media can be stored in wells of plate, tubes, or on MALDI target. In these embodiments, the solid support having analyte bound may also contain the MALDI matrix and/or mass internal standard or other components. These mixtures can be stored wet or dry (e.g. lyophilized). Suitable temperatures for column storage can range from −80° C. to 60° C. A person having ordinary skill in the art of MALDI-TOF MS sample preparation could readily determine the appropriate conditions for storage. In some embodiments, dark storage conditions are preferred.

In some embodiments of the invention, an automated process can be used to retrieve archived samples. For example, MALDI samples stored frozen in a 96-well plate can be thawed and arrayed onto a MALDI target using a liquid handling system such as the MEA personal purification System™ (PhyNexus, Inc., San Jose). In some embodiments, a computer is used to keep track of archived sample information.

The method of the invention provides a device comprising columns, tubes or wells containing a solid support, a pump attached to one end of said column, and an automated means for actuating the pump. Typically, the method is performed in parallel using a liquid handling robot to pump the solutions through the columns. The liquid handling system is controlled by a computer having a processor and software. This software controls the liquid handling system, and can be programmed to introduce desired liquids into a column, well, or tubes as well as to evacuate the liquid by the positive introduction of gas into the column if so desired. The preparation of the slurry and spotting of the slurry onto a MALDI target plate can also be performed with a computer controlled device, such as the MEA Personal Purification System™ (PhyNexus, Inc., San Jose).

Multiplexing

In some embodiments of the invention a plurality of columns is run in a parallel fashion, e.g., multiplexed. This allows for the simultaneous, parallel processing and spotting of multiple samples. In some embodiments, the method is applied concurrently and in parallel to multiple pipette tip columns sealingly attached to a multi-channel pipettor (such as a robotic liquid handling system), Multiplexing can be accomplished by use of the columns, wells or tubes using a pipetting robot or liquid handling system such as the MEA Personal Purification System™ from PhyNexus, Inc., San Jose. Example 8 includes instructions for operating the MEA Personal Purification System™ and the entire operating Manual is available from the PhyNexus website (http://www.phynexus.com/). Other liquid handling systems that can be used with the methods of the instant invention include those manufactured by Zymark (e.g., the SciClone sample handler), Tecan (e.g., the Genesis NPS, Aquarius or TeMo) or Cartesian Dispensing (e.g., the Honeybee benchtop system), Packard (e.g., the MiniTrak5, Evolution, Platetrack. or Apricot), Beckman (e.g., the FX-96) and Matrix (e.g., the Plate Mate 2 or SerialMate) and others. However any liquid handling system used with the methods of the instant invention must be adapted to include a MALDI target and alignment fixture.

Samples can be arrayed from a column to a predetermined location or a plurality of predetermined locations, for example locations on a MALDI target, chip or microwells in a multi-well plate. MALDI targets, which are used to deliver samples to a Mass Spectrometer for analysis by Matrix Assisted Laser Desorption Ionization (MALDI) can have at least 96 spots, and can have 384, or 1536 spots, however, it is also possible to analyze a MALDI target with fewer than 96 samples or spots. When samples are arrayed on a MALDI target, an alignment fixture can be used to ensure accurate placement of each sample on the target.

When using a multiplexed system, it may be desirable to program delays into the software controlling the protocol. When several columns are operated in parallel, each column may have a slightly different back pressure. As a result, the flow rate of a liquid through each column may vary when vacuum or pressure is applied to the columns. One means of compensating for the different flow rates is the incorporation of delays to equalize the vacuum or pressure and thus equalize the total amount of liquid expelled or aspirated. Pauses can be used at any time during the protocol, e.g. while aspirating, dispensing, or between an aspiration and a dispense step.

In one example of a multiplexing procedure, 10 Eppendorf tubes containing a sample, e.g., 5 µL of serum containing cancer marker proteins are placed in the sample rack. One mL syringes are attached to the syringe holder, and the plungers are engaged with the plunger holder. Columns, such as those described elsewhere herein, are affixed to the syringe attachment fittings. The column is conditioned by ejecting the bulk of the storage solution and replacing it with air. The sample rack is raised so that the ends of the columns enter the sample. Sample solution is drawn into the columns by action of the syringe pump, which raises the plunger holder and plungers. The pump is preferably capable of precisely drawing up a desired volume of solution at a desired flow rate, and of pushing and pulling solution through the column. An example of a suitable syringe pump is the MEA (available from PhyNexus, Inc., San Jose, Calif.). Control of the solvent liquid in the column is optionally bidirectional. In this case, and where a syringe is used to control the liquid, the syringe plunger head and the syringe body should be tightly held within the syringe pump. When the syringe plunger direction is reversed, then there can be a delay or a hysteresis effect before the syringe can begin to move the liquid in the opposite direction. This effect becomes more important as the volume solvent is decreased. In the MEA instrument, the syringe and syringe plunger are secured so that no discernable movement can be made against the holder rack.

If the sample volume is larger than the interstitial volume of the bed, sample is drawn through the solid support and into the column body. The sample solution is then expelled back into the sample container. In some embodiments, the process of drawing sample through the solid support and back out into the sample container is performed two or more times, each of which results in the passage of the sample through the solid support twice. As discussed elsewhere herein, analyte adsorption can in some cases be improved by using a slower flow rate and/or by increasing the number of passages of sample through the media.

The sample container is then removed and replaced with a similar container holding wash solution (e.g., in the case of a preparation utilizing an immobilized metal, PBS or similar buffer), and the wash solution is pumped back and forth through the solid support (as was the case with the sample). The wash step can be repeated one or more times with additional volumes of wash solution. A series of two or more different wash solutions can optionally be employed, e.g., PBS or buffer followed by water.

After the wash step, the solid support can optionally be purged with gas to remove bulk solution from the interstitial space. Optionally, the syringe can be changed prior to slurry preparation and spotting. For example, 200 µL disposable syringes used for sample and wash solution can be replaced with 20 µL GasTight syringes. An aliquot of slurry solvent is placed at the bottom of each column (e.g., 10 µL would be typical for slurry prepared from an immobilized metal column having a bed size of about 1 mg). The slurry solution can be manipulated back and forth through the bed multiple times by repeated cycles of aspirating and expelling the solution through the column. The final cycle is completed by spotting the slurry onto the MALDI target.

The above-described preparation process can be automated, for example by using software to program the computer controller to control the pumping, e.g., the volumes, flow rates, delays, and number of cycles.

In some embodiments, the invention provides a multiplexed preparation system comprising a plurality of columns of the invention, e.g., pipet tip columns having small beds of solid support or resin. For some embodiments the invention provides a multiplexed slurry preparation system comprised of pipette tips, a slurry solvent and solid support from the columns. After the slurry has been prepared for some embodiments, the invention provides a multiplexed spotting of the slurry onto the MALDI target comprising a plurality of pipette tips and plurality of slurries each containing the analyte(s). The pipette tips pick up the slurry and spot the material onto the MALDI target. Any remaining slurry is retained for archiving. The spotted MALDI target is dried and mass spectrometry analysis performed.

The system can include a pump or pump in operative engagement with the columns, useful for pumping fluid through the columns in a multiplex fashion, i.e., concurrently. In some embodiments, each column is addressable. The term "addressable" refers to the ability of the fluid manipulation mechanism, e.g., the pumps, to individually address each column. An addressable column is one in which the flow of fluid through the column can be controlled independently from the flow through any other column which may be operated in parallel. In practice, this means that the pumping means in at least one of the steps is in contact and control of each individual column independent of all the other columns. For example, when syringe pumps are used, i.e., pumps capable of manipulating fluid within the column by the application of positive or negative pressure, then separate syringes are used at each column, as opposed to a single vacuum attached to multiple syringes. Because the columns are addressable, a controlled amount of liquid can be accurately manipulated in each column. In a non-addressable system, such as where a single pump is applied to multiple columns, the liquid handling can be less precise. For example, if the back pressure differs between multiplexed columns, then the amount of liquid entering each column and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

The invention also provides software for implementing the methods of the invention. For example, the software can be programmed to control manipulation of solutions and addressing of columns into sample vials, collection vials, for spotting or introduction into some analytical device for further processing.

The invention also includes kits comprising one or more reagents and/or articles for use in a process relating to solid-phase extraction, e.g., buffers, standards, solutions, columns, sample containers, etc.

Purification of Classes of Proteins

Columns can be used to purify entire classes of proteins on the basis of highly conserved motifs within their structure, whereby an affinity binding agent is used that reversibly binds to the conserved motif. For example, it is possible to immobilize particular nucleotides on the column media. These nucleotides include adenosine 5'-triphosphate (ATP), adenosine 5'-diphosphate (ADP), adenosine 5'-monophosphate (AMP), nicotinamide adenine dinucleotide (NAD), or nicotinamide adenine dinucleotide phosphate (NADP). These nucleotides can be used for the purification of enzymes that are dependent upon these nucleotides such as kinases, phosphatases, heat shock proteins and dehydrogenases, to name a few.

There are other affinity groups that can be immobilized on the media for purification of protein classes. Lectins can be employed for the purification of glycoproteins. Concanavilin A (Con A) and lentil lectin can be immobilized for the purification of glycoproteins and membrane proteins, and wheat germ lectin can be used for the purification of glycoproteins and cells (especially T-cell lymphocytes). Though it is not a lectin, the small molecule phenylboronic acid can also be immobilized and used for purification of glycoproteins.

It is also possible to immobilize heparin, which is useful for the purification of DNA-binding proteins (e.g. RNA polymerase I, II and III, DNA polymerase, DNA ligase). In addition, immobilized heparin can be used for purification of various coagulation proteins (e.g. antithrombin III, Factor VII, Factor IX, Factor XI, Factor XII and XIIa, thrombin), other plasma proteins (e.g. properdin, BetaIH, Fibronectin, Lipases), lipoproteins (e.g. VLDL, LDL, VLDL apoprotein, HOLP, to name a few), and other proteins (platelet factor 4, hepatitis B surface antigen, hyaluronidase). These types of proteins are often blood and/or plasma borne. Since there are many efforts underway to rapidly profile the levels of these types of proteins by technologies such as protein chips, the performance of these chips will be enhanced by performing an initial purification and enrichment of the targets prior to protein chip analysis.

It is also possible to attach protein interaction domains to media for purification of those proteins that are meant to interact with that domain. One interaction domain that can be immobilized on the media is the Src-homology 2 (SH2) domain that binds to specific phosphotyrosine-containing peptide motifs within various proteins. The SH2 domain has previously been immobilized on a resin and used as an affinity reagent for performing affinity chromatography/mass spectrometry experiments for investigating in vitro phosphorylation of epidermal growth factor receptor (EGFR) (see Christian Lombardo, et al., Biochemistry, 34:16456 (1995)). Other than the SH2 domain, other protein interaction domains can be immobilized for the purposes of purifying those proteins that possess their recognition domains. Many of these protein interaction domains have been described (see Tony Pawson, Protein Interaction Domains, Cell Signaling Technology Catalog, 264-279 (2002)) for additional examples of these protein interaction domains).

As another class-specific affinity ligand, benzamidine can be immobilized on the solid support for purification of serine proteases. The dye ligand Procion Red HE-3B can be immobilized for the purification of dehydrogenases, reductases and interferon, to name a few.

In another example, synthetic peptides, peptide analogs and/or peptide derivatives can be used to purify proteins, classes of proteins and other biomolecules that specifically recognize peptides. For example, certain classes of proteases recognize specific sequences, and classes of proteases can be purified based on their recognition of a particular peptide-based affinity binding agent.

Multi-Protein Complexes

In certain embodiments, the columns of the invention are used to extract and/or process multi-protein complexes. This is accomplished typically by employing a sample solution that is sufficiently non-denaturing that it does not result in disruption of a protein complex or complexes of interest, i.e., the complex is extracted from a biological sample using a sample solution and conditions that stabilize the association between the constituents of the complex. As used herein, the term multi-protein complex refers to a complex of two or more proteins held together by mutually attractive chemical forces, typically non-covalent interactions. Covalent attachments would typically be reversible, thus allowing for recovery of component proteins.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

Example 1

Preparation of IDA-$Cu^{2+}$-Cellulose $Cu^{2+}$ was loaded on derivatized cellulose particles. To derivatize cellulose 10 g of Celluflow C-25 (8 μM particles, Collaborative Laboratories, New York) were dispersed with strong agitation in 230 ml of water for 2 minutes. 328 mM of monomer glycidyl methacrylate was added and the reaction mixture took place for 2 hours at 70° C. with 6.5 mM of ammonium persulfate and 8.6 mM of sodium thiosulfate as redox catalysts. The polymerization and grafting reaction was finalized by raising the temperature to 80° C. for 2 hours. The suspension was then filtered and washed with a large volume of deionized water.

The residual cellulose matrix was dispersed in 113 mM iminodiacetic acid (IDA) solution, prepared by dissolving IDA in 200 ml of a 2 M sodium carbonate solution followed by the addition of 86 mM of sodium chloride for 5 hours at 75° C. with vigorous stirring. The final product was vacuum-filtered, washed with deionized water and saturated with the designated $Cu^{2+}$ ions by incubation of the derivatized cellulose with 50 mM metal solution for at least 2 hours at room temperature.

Figure 2:
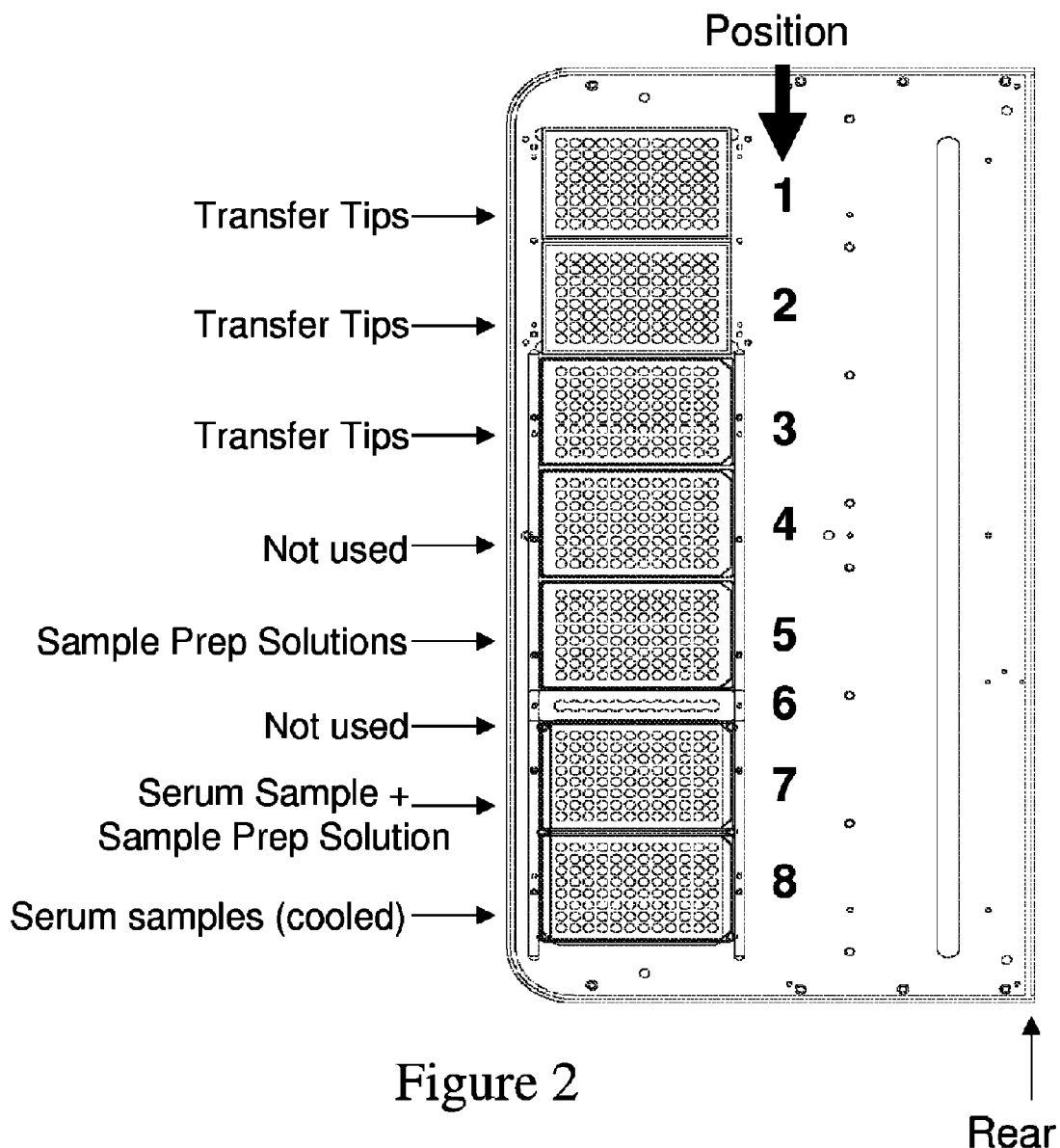
FIG. 2 is a depiction of the set-up of the MEA Personal Purification System™ for serum sample preparation.

1.5 mg of the respective IDA-$Cu^{2+}$-cellulose was filled in a 200 μL PhyTip® column. Therefore, 20 mg of cellulose particles were suspended in 1.5 ml of 50 mM of sodium acetate buffer and aliquots of 100 μl were filled in 12 PhyTip® columns. The excess liquid was expelled and the tips were placed at position 2, row 1 of the MEA™ instrument (FIG. 2).

Example 2

Automated Serum Sample Preparation

Serum samples of histological confined prostate cancer and age matched unaffected healthy men (50 years old, PSA 0.5 ng/ml) were provided by the Department of Urology, at the Medical University of Innsbruck, Austria. Raw serum samples were treated with buffer and surfactant to prepare them for the MELDI analytical process. A schematic of the MEA Personal Purification System™ layout is shown in FIG. 2 and described below.

1. MEA instrument is loaded with 3 boxes of transfer tips at positions 1-3. Serum samples (up to 15 μL) are placed in position 8 (cooled.) Sample preparation solutions A, B, and C are placed in rows A, B and C of a deep well plate in position 5.
2. Using a row of tips from position 1, 5 μL of sample preparation solution A, (8 M urea containing 1% 3-[(3-cholamidopropyl)dimethylammonio]-1-propane sulfonate (CHAPS) in phosphate buffered saline (PBS)), is added to each serum sample at position 7 and mixed using 3 cycles of intake/expel at 500 μL/min. Tips are replaced in position 1.
3. Using tips from position 2, 10 μL of sample preparation solution B, 1 M urea containing 0.125% CHAPS, is added to product from step 2 at position 7 and mixed using 3 cycles intake/expel at 500 μL/min. Tips are replaced in position 2.
4. Using tips from position 3, 80 μL of sample preparation solution C, PBS, is added to the product from step 3 at position 7 and mixed using 3 cycles intake/expel at 500 μL/min. Tips are replaced in position 3.
5. Up to 8 rows of samples are processed a row at a time with all 3 steps.
6. The plate of up to 96 samples is ready to be processed with the MELDI PhyTip columns.

Example 3

Automated on-Column Sample Preparation

Figure 3:
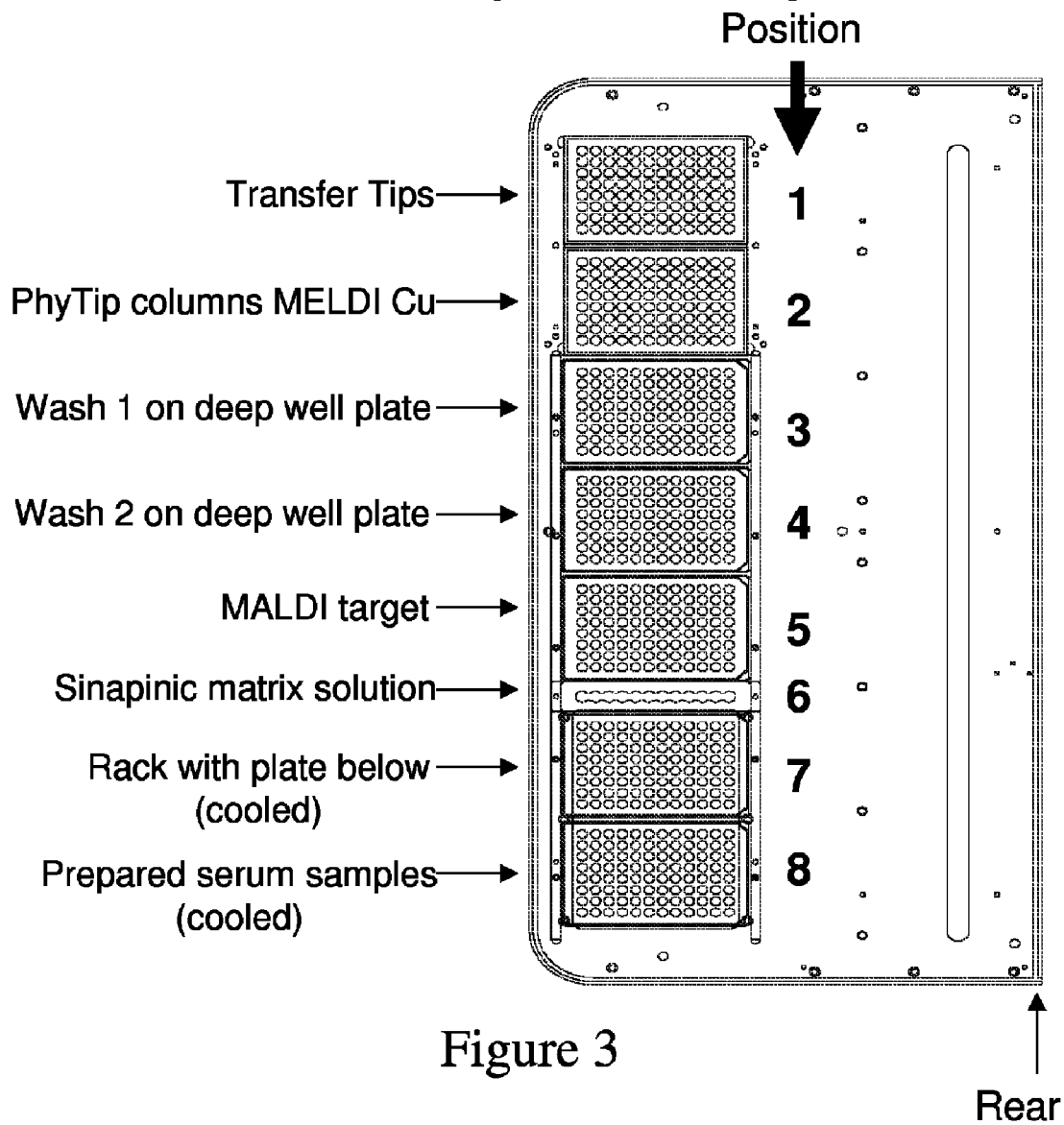
FIG. 3 is a depiction of the set-up of the MEA Personal Purification System™ for sample processing.
Figure 4:
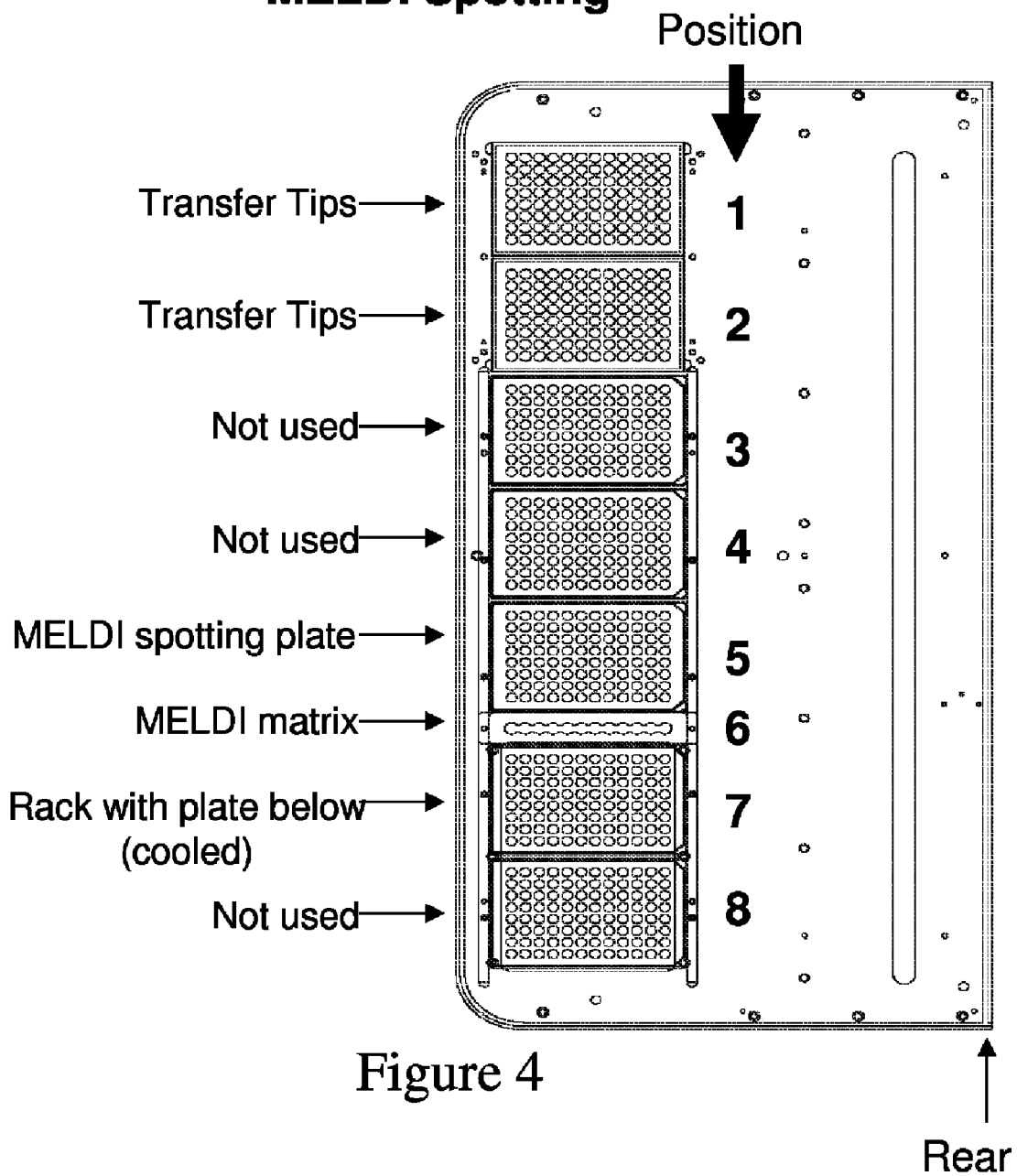
FIG. 4 is a depiction of the set-up of the MEA Personal Purification System™ modified for spotting on the MALDI target.
Figure 12:
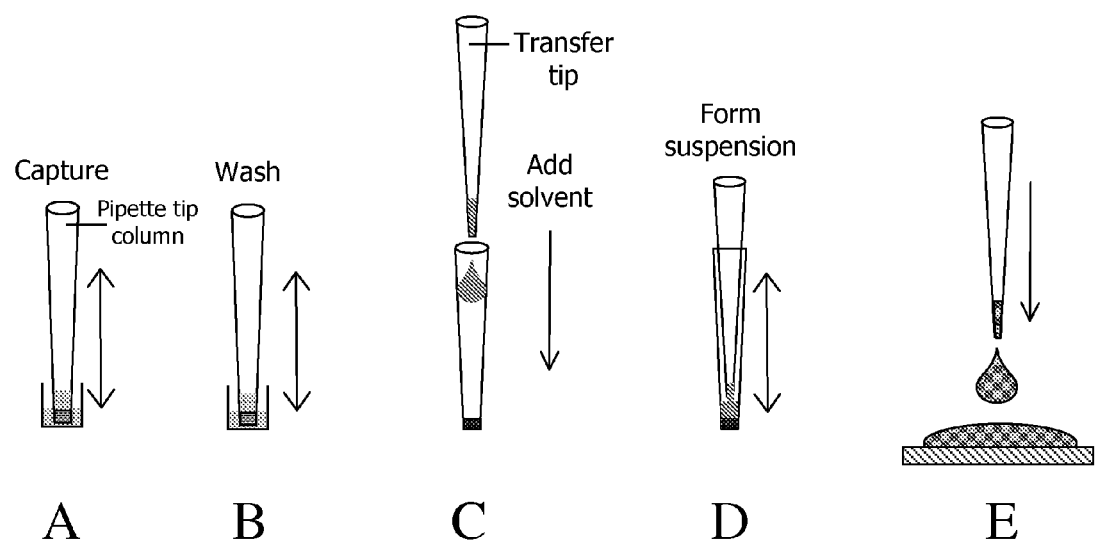
FIG. 12 is a depiction of the method performed in Example 3.

Prepared serum samples are processed MELDI cellulose material with PhyTip® columns with an automated process. A schematic of the MEA Personal Purification System™ layout is shown in FIGS. 3, 4 and 12. The procedure is described below.

1. MEA Instrument is loaded with a box of tips at position 1, a box of MELDI Cu2+-IDA-cellulose columns at position 2, a wash plate containing wash 1 (PBS) at position 3, a wash plate containing wash 2 (DI water) at position 4, a MALDI target at position 5, sinapinic matrix solution (20 mg/ml in 50% acetonitrile and 0.1% TFA) in the 12 well tray at position 6, and a plate of prepared serum samples from Example 2 at position 8.
2. A row of MELDI-Cu2+-IDA-cellulose column are picked up and washed with ultra pure water for 5 cycles of 100 µl intake/expel at 1 ml/min at position 4.
3. The washed columns are then conditioned at position 3 with PBS buffer for 5 cycles of 100 µl intake/expel at 1 ml/min.
4. The conditioned columns are picked up and the sample is loaded at position 8, 10 cycles of intake/expel at 250 µl/min and excess liquid is blown out (FIG. 12A).
5. The Cu2+-IDA-cellulose resins in the column is washed at positions 3 and 4 for 5 cycles each of intake/expel at 250 µL/min and excess liquid is blown out (FIG. 12B). After washing, the column with the moist bed is placed into the rack at position 7 with the tip in the cool well to keep bed moist.
6. Using a row of tips from position 1, 20 µL of matrix solution containing 20 mg/ml sinapinic acid in 50% acetonitrile and 0.1% trifluoroacetic acid from position 6 is added to the top of a row of columns in rack at position 7 (FIG. 12C). A suspension is formed by passing the cellulose and liquid back and forth into the transfer tip 4 cycles of intake/expel at 1 mL/min (FIG. 12D). The row of tips is raised from the columns and 6 µL of air is drawn into the tip. The row of tips is placed back into the slurry suspension in the column and a 2 µL aliquot of slurry is drawn up into the transfer tip.
7. The row of transfer tips containing the resin-matrix slurry is moved to position 5 over the alignment fixture and MALDI target (FIGS. 4 and 7), lowered and 2 µl of material is spotted onto the MALDI target (FIG. 12E and FIG. 8).
8. The plate is air dried and analyzed by Mass Spectrometry.

Example 4

MALDI-TOF-MS Analysis

Proteins bound to the derivatized cellulose and spotted onto the plate were analyzed by MALDI-TOF-MS (Ultraflex MALDI-TOF-TOF, Bruker Daltonics, Bremen, Germany). All serum samples were automatically measured in linear mode using the following settings: ion source; ion source 2; lens; pulsed ion extraction, nitrogen pressure. Ionization was achieved by irritation with a nitrogen laser operating at 50 Hz. For matrix suppression a high gating factor with signal suppression of 600 Da was used. External mass calibration was performed with a protein standard mixture from Bruker Daltonics covering the mass range from 1000 to 20,000 Da. Each sample was measured in triplicate and for each spot 600 spectra were acquired (100 laser shots at different positions). All spectra were recorded with the aid of AutoXecute tool of flexControl acquisition software in a mass range of 1000 to 20,000 Da. Data were collected by averaging 600 laser shots and analyzing mass region from 2000 to 12,000 Da. The validation of all data obtained was carried out by using Flex analysis 2.2 post analysis software and for data acquisition by Flex control 2.2.

Example 5

MALDI Data Analysis

Figure 5:
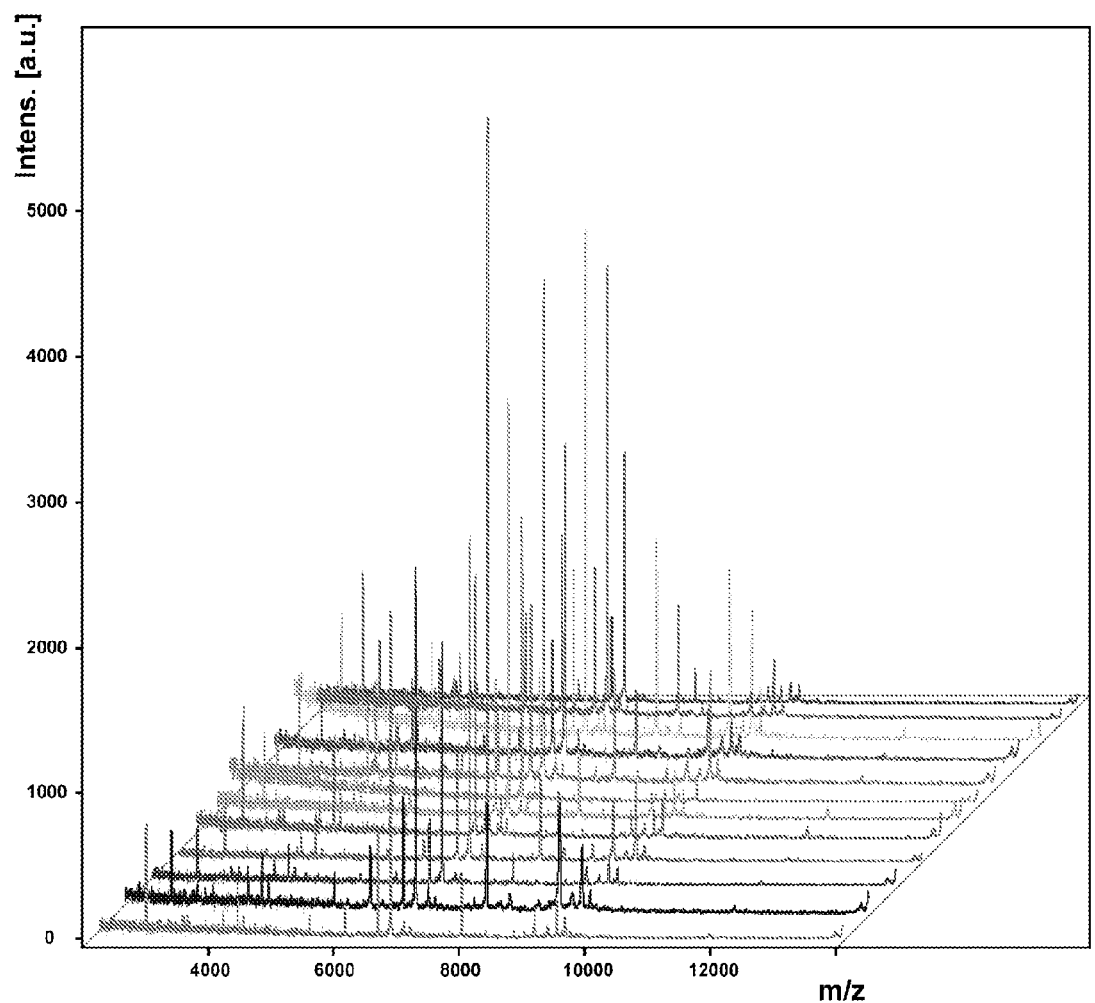
FIG. 5 shows twelve representative spectra from 12 aliquots of one serum.

The reproducibility was proved by automated sample preparation and analysis of 12 aliquots of one given serum. Twelve representative spectra were then recorded (FIG. 5). MALDI-protein profiles of these 12 representative spectra showed consistent peaks at distinct positions (of distinct masses) and clearly showed a stable spectrum, when using this analytical technique.

Example 6

Use of an Internal Mass Standard

Serum samples were prepared as in Example 3 except that the matrix solution in position 6 additionally contained 100 fmol each of angiotensin I and cytochrome C for internal calibration. Each sample was spotted on four different positions on the MALDI plate. The mass spectrometer was mass calibrated with 3 masses from the protein standard during various times during the analysis.

Example 7

Analysis of Archived Samples

The slurry remaining in the columns from Example 3 was archived for future analysis by MS or other analytical methods by placing the rack of columns containing slurry into the freezer. After 1 month, samples were selected and run analyzed by Mass Spectrometry. The proteins detected were identical to those detected in the first analysis from Example 4.

Example 8

Use of the PhyTip® MEA Purification System

1. Setting the Instrument Deck
The instrument deck can be configured in a number of different ways, but one standard configuration is as follows: On the left there are two positions for Tip boxes and to the right of these, there is enough space to hold 5 plates (standard SBS) and one reagent reservoir.
Position 1. PhyTip Box
Position 2. PhyTip Box
Position 3. Plate position (Plate 1)
Position 4. Plate position (Plate 2)
Position 5. Plate position (Plate 3)
Position 6. Reservoir position
Position 7. Plate position (Plate 4)
Position 8. Plate position (Plate 5)
If necessary, the positions of these plates can be changed by moving the attached pins and replacing them in the appropriate positions. This maintains perfect alignment of each plate in each position during MEA operation.

Example

Position 1

PhyTip Columns

For the MEA system, these should only be the appropriate PhyTip columns for the 12 channel system that is being used, e.g. 200+ or 1000+, and the resin that is required.

Position 2

Empty Box for Used PhyTip Columns

Used PhyTip columns can be replaced in their original box or if required, in a separate empty box.

Position 3

Extra Plate Position

This extra position can be used for a number of different applications e.g. extra wash step etc.

Position 4

Wash Plate 1

Depending on the specific application, a number of different types of wash plates or fixtures may be placed in this position, e.g. deep well 96-well plates. Care must be taken when choosing the type of deep well 96-well plate. When using the 1000+ system, PhyNexus recommends the use of 2 mL, square well plates (PhyNexus Part Number PCP 96-20-10).

Position 5

Wash Plate 2

Depending on the specific application, a number of different types of wash plates or fixtures may be placed in this position, e.g. deep well 96-well plates. Care must be taken when choosing the type of deep well 96-well plate. When using the 1000+ system, PhyNexus recommends the use of 2 mL, square well plates (PhyNexus Part Number PCP 96-20-10).

Position 6

Reservoir Position

Depending on the application and specific affinity resin used, the Reservoir Position can be used as a holder for slurry buffer. When used in this mode, the reservoir is filled with sufficient volume of buffer. Also Tip box position 2 should be used to hold standard Rainin LTS Pipette Tips.

Position 7

Sample Plate (Samples)

Depending on the specific application, a number of different types of sample plates may be placed in this position, e.g. deep well 96-well plates.

Position 8

Elution Plate

PhyNexus recommends the use of the PhyTip Elution Plates (Part number PCP 96-00-10) for the final step of elution. These plates have v-bottoms which maximize the process of elution. It is also recommended to cover the plates, once the elution buffer has been added, with a PhyTip Plate Cover (Part number PCP 96-10-20) and PhyTip Plate Holder (Part number PCP 96-10-50). With the cooling accessory attached, both positions 7 and 8 can be maintained at sub ambient temperatures.

Quick Software Instructions

The Auto controller Operating Software has been designed for simple to use automated methods that have been preprogrammed into the system. However, any combination of movements and positions can be built into a user defined method. To begin, PhyNexus recommends that the user start with the built-in methods and subsequently modify these to match the requirements of the application.

Methods manage the entire process of moving the robotics tower with 12 channel system attached to perform the Capture, Purify and Enrich process for all of the defined samples, Protocols manage the individual steps of the Capture, Purify and Enrich process. A method is a series of protocols and robotic movement/position instructions that fully automate the entire process of purifying a full plate of 96 samples. To load the software onto a PC, simply insert the CD into the CD or DVD drive of the PC and follow the installation instructions on the screen.

For simplest use of the system, run the preprogrammed methods for any of the given affinity resins. To do this, go to File, then Open. This will bring down a screen that shows either Method or Protocol, click on Method to show all of the stored Methods. Open the standard method IMAC; this will bring down the operational screen. Now go to Method and click on Edit; this will show all of the individual steps of the method.

Click on any one of the individual steps of the methods to show the options screen; this will be split into two sections. The top section deals with the operation of the 12 channel system (controller), while the bottom section deals with robotics movement of the autocontroller. Actions that are available are:

Top Section:

Execute: executes a stored protocol, e.g. Capture

Audible Alert: introduces an audible alert at the end of an action

Home (controller): homes the 12 channel system to a zero volume

Pause for Operator: builds in an automatic pause in the method

Comment: allows operator to build in an automatic comment or prompt between actions Blowout: causes a 12 channel system to blow out any air from the syringe Example 9

Poly(GMA/DVB) Particle Preparation and Derivatization

Glycidyl methacrylate (GMA) was copolymerized with divinylbenzene (DVB) following the polymerization protocol described by Aprilita et al (J. Proteome Res. 2005; 4: 2312. DOI: 10.1021/pr050224m S1535-3893(05)00224-1). The polymerization process was carried out under stirring and non-stirring conditions to achieve support materials of different particle sizes and pores.

Example 10

Derivatization with IDA—Immobilized Metal Affinity Chromatography (IMAC) poly(GMA/DVB)-IDA-$Cu^{2+}$ The particles obtained from Example 9 were derivatized with IDA under alkaline conditions. After filtration and several washing steps the product was loaded with $Cu^{2+}$ by incubation with 100 mM $CuSO_4$ solution for 2 h at room temperature.

Example 11

Derivatization with Octadecylamine—Reversed Phase (RP) poly(GMA/DVB)-RP

Poly(GMA/DVB) (4 g) from example 9 was suspended in acetonitrile (150 mL) in a round-bottomed flask equipped with a magnetic stirrer, condenser, thermometer and nitrogen inlet. Then, octadecylamine (5 g) was added and the mixture was heated up to 80° C. for 6 h with continuous stirring. The mixture was cooled to room temperature, separated by centrifugation and washed with acetonitrile.

Example 12

Derivatization with Triethylamine-Anion Exchanger (AX) poly(GMA/DVB)-AX

Poly(GMA/DVB) (4 g) from example 9 was added into a round-bottomed flask equipped with a magnetic stirrer, condenser, thermometer and nitrogen inlet. Additionally, triethylamine (150 mL) was added. The mixture was heated up to 90° C. for 16 h with continuous stirring and nitrogen purge. The particles were washed with methanol and deionized water.

Example 13

Surface Chemistry Comparison

The different poly(GMA/DVB) derivatives obtained in Examples 10, 11 and 12 are compared with respect to their binding potential of peptides and proteins from human serum samples. For each solid support material, human serum is processed and MALDI-TOF mass spectra are obtained as described in examples 2, 3 and 4. The protein profile for poly(GMA/DVB)-IDA-$Cu^{2+}$ shows more peaks than those for poly(GMA/DVB)-RP and poly(GMA/DVB)-AX suggesting higher binding capacity. However, there are some protein mass peaks present in the poly(GMA/DVB)-AX and poly(GMA/DVB)-RP that are absent in the poly(GMA/DVB)-IDA-$Cu^{2+}$ profile suggesting maximum information is obtained from serum samples by utilizing all three protein profiles.

Example 14

Gel Maps of Five MELDI Measurements

Gel maps of five independent MELDI measurements were obtained from one serum sample that was prepared and spotted as described in Example 3. The ion peaks were consistent for all five runs.

Example 15

Figure 9:
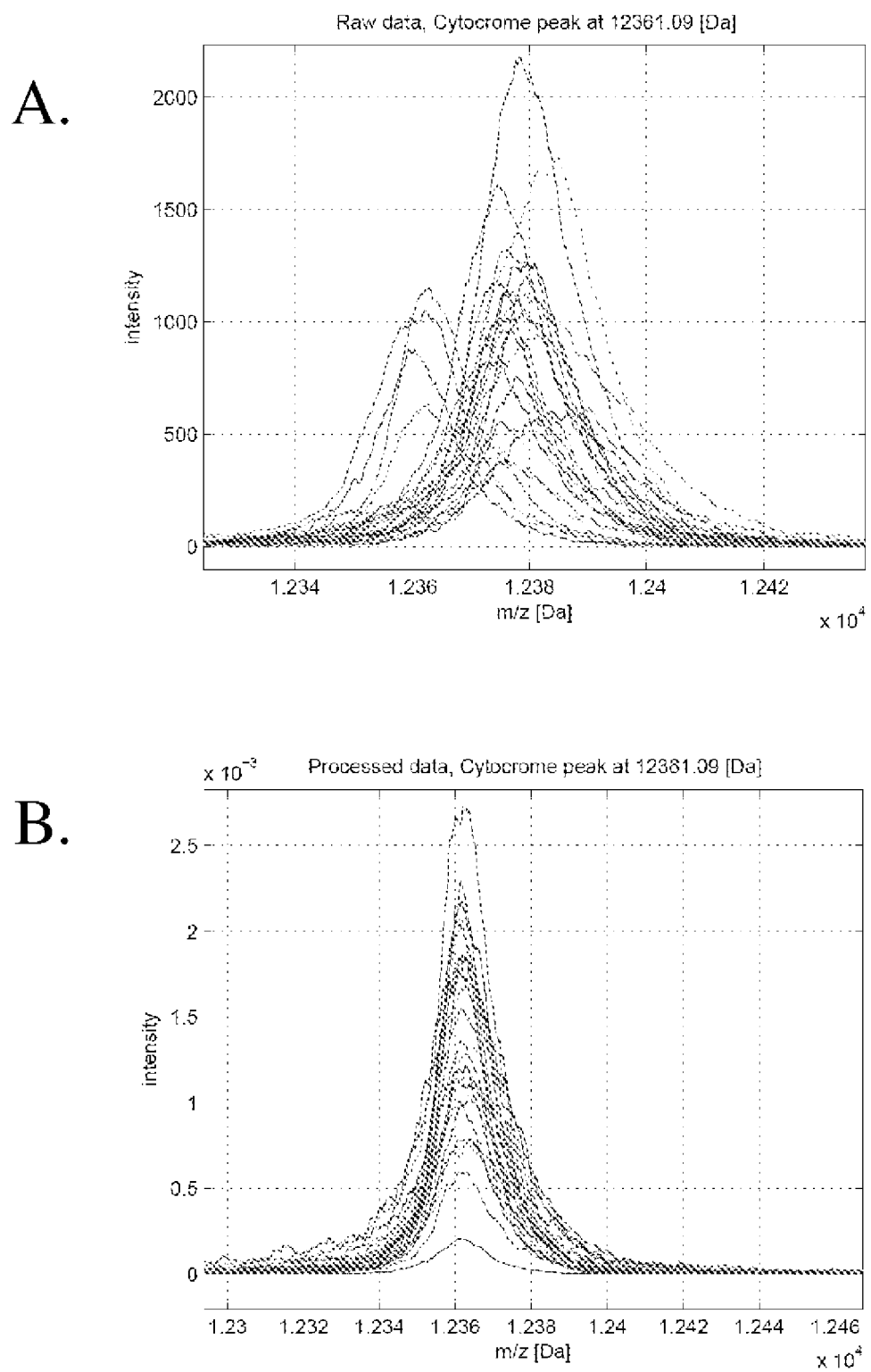
FIG. 9A shows serum proteins analyzed from 24 columns by MALDI-TOF-MS as described in Example 15.
FIG. 9B shows the protein profiles of FIG. 9B following alignment.

Comparison of Multiple On-Column Sample Preparations $Cu^{2+}$ was loaded onto derivatized IDA cellulose particles and twenty-four, 200 µl PhyTip® columns were filled as described in Example 1. One serum sample was prepared as described in Example 2 and processed in the twenty-four PhyTip® columns as described in Example 3. The serum proteins were analyzed by MALDI-TOF-MS (FIG. 9A) and the protein profiles were aligned (FIG. 9B). A comparison of the gel maps using the mass internal standard showed consistent peak intensities over the twenty-four serum preparations.

Example 16

Comparison of Mass Internal Standards

Figure 10:
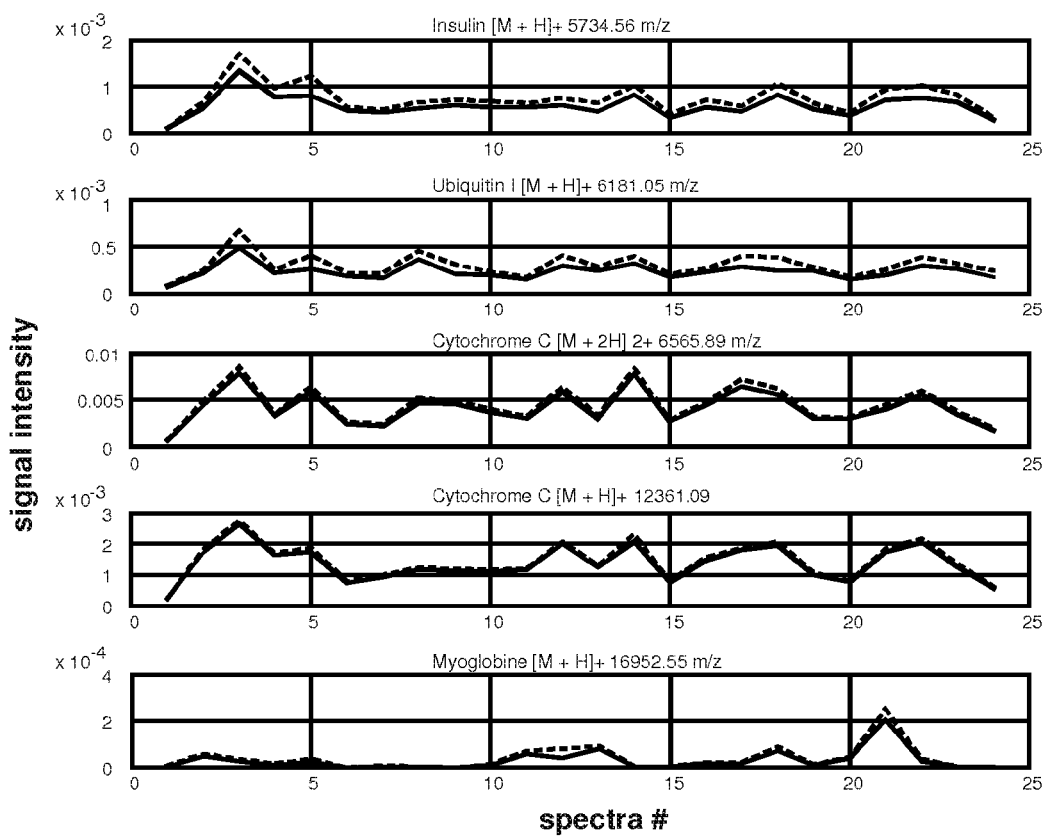
FIG. 10 shows the signal intensities of five mass internal standards described in Example 16.

To identify a suitable mass internal standard for normalization of signal intensity across multiple samples or sample preparations, five candidate mass internal standards were added to each preparation described in Example 15 and their signal intensities were compared. The five mass internal standards were: insulin [M+H]+5734.56 m/z, ubiquitin [M+H]+ 6181.05 m/z, cytochrome C [M+2H]2+6565.89 m/z, cytochrome C [M+H]+12361.09 m/z, and myoglobin [M+H]+ 16952.55 m/z. All proteins except myoglobin showed sufficient signal intensity in all twenty-four sample preparations to serve as a useful internal mass standard (FIG. 10).

Example 17

Hepatocellular Carcinoma Cell Lysate Preparation

The hepatocellular carcinoma (HCC) cell lines termed as phenylketonuria (PKU)-hep-11 and -hep-12 were established from a 48-year-old HCC patient at different clinical stages and cultured in DMEM, supplemented with 10% FCS. To prepare the sample, the cells were rinsed three times in PBS and collected into 1.5 mL tubes. The cell pellets were resuspended in lysis buffer (8 M urea, 4% CHAPS, 40 mM Tris, 65 mM DTT, 2% Bio-Lytes1) and centrifuged at 25,000×g for 1 h at 48° C. Protein concentrations were determined using the Bradford assay. All samples were stored at −80° C. prior to analysis.

Example 18

QC Method for MELDI Material

A. Determination of Metal Capacity
Loading of IDA-Cellulose with Cu2+-Ions

IDA-cellulose particles were suspended in 100 mM $CuSO_4$ (30 ml/g IDA cellulose particles) and mixed at ambient temperature for one hour. Afterwards, the excess $Cu^{2+}$ was removed washing the particles with 20 ml of $H_2O$, followed by a quick washing step with 30 ml of 500 mM NaCl and finally again with 20 ml of $H_2O$. The filtered and washed product was then dried over blue gel.

Elution of Immobilized Cu2+-Ions

An exact selected mass of the respective IDA-$Cu^{2+}$-cellulose was suspended in 2 ml 50 mM $Na_2EDTA$ solution and mixed for 10 min at 1500 rpm. The suspension was then centrifuged at 1300 rpm for 5 min. After centrifugation, the supernatant was transferred in a graduated flask (5-20 ml) and the procedure was repeated once more. Finally the supernatants were combined in the graduated flask, which was then filled up with 50 mM $Na_2EDTA$ solution.

Atom Absorption Spectrometry.

The Cu-EDTA solution was first diluted to a final concentration of $1.6 \times 10^{-4}$ M (~10 ppm) and analyzed at 324.6 nm.

External calibration was performed by measuring 6 standard solutions of a concentration of 4-12 ppm. Finally the metal capacity (μg/g) was determined by means of the calibration curves.

B. Usability for MELDI

One human serum was processed 8 times using the MEA MELDI methods for MS protein profiling. The metal capacity was 350 μmol/g.

MELDI Measurements

Figure 11:
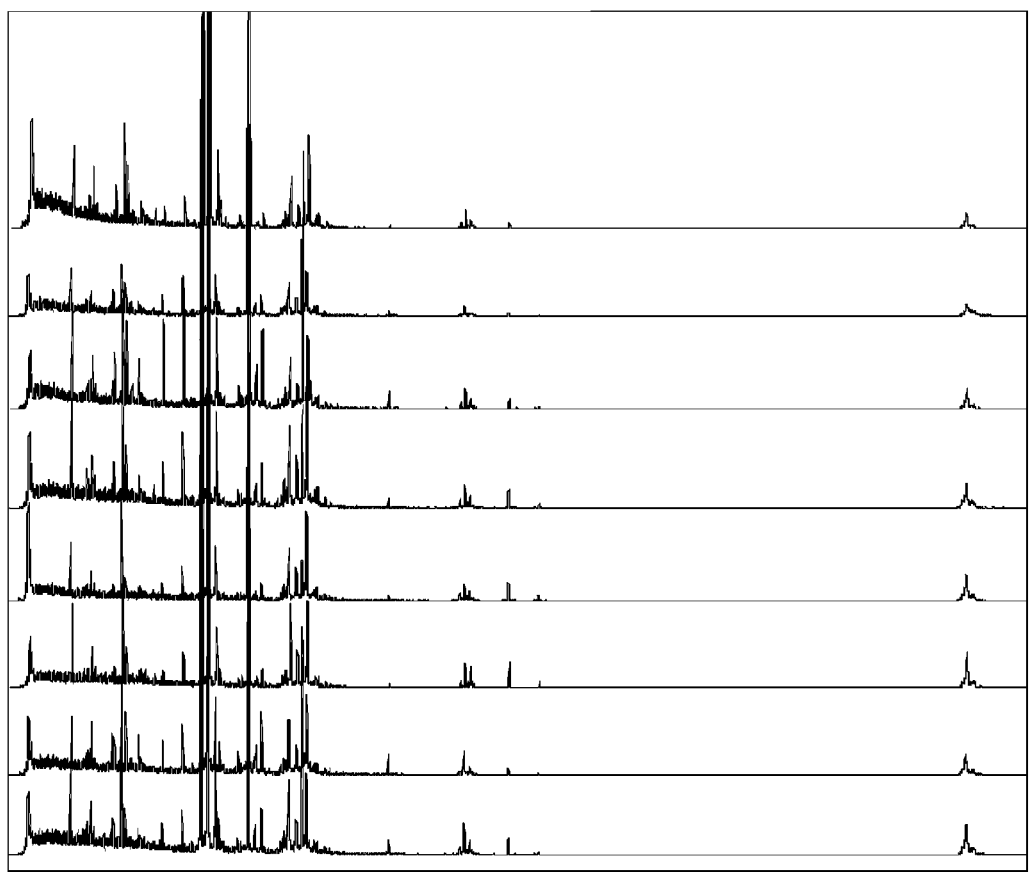
FIG. 11 shows the mass spectra of a human serum processed 8 times using the MEA MELDI methods.

Samples were measured on a Ultraflex I in linear mode, averaging 600 Laser shots. All spectra were recorded with the aid of the AutoXecute tool of flexControl acquisition software analyzing the mass range of 1000 to 30,000 m/z (FIG. 11).

We claim:

1. An automated method for preparing an analyte from a sample for mass spectrometry comprising:
   a) providing at least one pipette tip column in operative engagement with a liquid handling system, wherein the pipette tip column is comprised of
      i) a column body having an open upper end, an open lower end, and an open channel between the upper and lower ends of the column body,
      ii) a bottom frit extending across the open channel, and
      iii) a bed of media positioned inside the open channel and in contact with the bottom frit;
   b) introducing a sample containing an analyte into the pipette tip column whereby the analyte is captured on the solid support;
   c) introducing a wash solution into the pipette tip column;
   d) optionally, repeating step (c);
   e) ejecting the pipette tip column from the liquid handling system;
   f) introducing a solvent into the open upper end of the pipette tip column with a transfer tip;
   g) aspirating and expelling the solid support and the solvent through the lower end of a transfer tip to produce a suspension;
   h) aspirating the suspension into the transfer tip from the open upper end of the pipette tip column;
   i) depositing the slurry onto a MALDI target; and
   j) at least partially drying the slurry on the MALDI target.

2. The method of claim 1 wherein a MALDI matrix is added prior to step (d) and wherein the slurry is further comprised of the MALDI matrix.

3. The method of claim 2 wherein a mass internal standard is added prior to step (d) and wherein the slurry is further comprised of the mass internal standard.

4. The method of claim 1 wherein a mass internal standard is added prior to step (d) and wherein the slurry is further comprised of the mass internal standard.

5. The method of claim 1 wherein following step (e) or step (f), a MALDI matrix is deposited over the slurry on the MALDI target.

6. The method of claim 1 wherein the solid support having an analyte bound is removed from the pipette tip column following step (b).

7. The method of claim 1 wherein the solid support is selected from the group consisting of normal phase, reverse phase, ion exchange, chelator, affinity and molecular sieve.

8. The method of claim 1 wherein the analyte is a biomolecule selected from the group consisting of proteins, peptides, phosphopeptides, polynucleotides, carbohydrates, lipids, nucleic acids, metabolites, polysaccharides, and small organic molecules.

9. The method of claim 1 wherein the solid support is selected from the group consisting of gel resins, pellicular resins, microporous resins, fibrous resins, molecular sieve resins, macroporous resins, silica, zirconium and titanium.

10. The method of claim 1 wherein the sample is selected from a group consisting of blood, urine, serum, tissue, tissue culture and cell culture.

11. The method of claim 1 wherein prior to step (e), the analyte is mixed with water, buffer or MALDI matrix and stored at a temperature between $-80°$ C. and $60°$ C. for a period of time prior to mass spectrometry.

12. The method of claim 1 wherein following step (f), the MALDI target is stored at a temperature between $-80°$ C. and $60°$ C. for a period of time prior to mass spectrometry.

13. The method of claim 1 wherein the sample is passed back and forth through the pipette tip column repeatedly.

* * * * *